United States Patent [19]

Helmer et al.

[11] Patent Number: 5,073,677
[45] Date of Patent: Dec. 17, 1991

[54] HERBICIDAL TOLERANT PLANTS CONTAINING RAT GLUTATHIONE S-TRANSFERASE GENE

[75] Inventors: Georgia Helmer, Apex, N.C.; John Duesing, Reihen, Switzerland; Steven Rothstein, Chapel Hill, N.C.; Liliana Scarafia, Chapel Hill, N.C.; Mary-Dell Chilton, Raleigh, N.C.; Hui-Chen J. Lai; Chen-Pei D. Tu, both of State College, Pa.

[73] Assignees: Ciba-Geigy Corporation, Ardsley, N.Y.; The Pennsylvania Research Corporation, University Park, Pa.

[21] Appl. No.: 391,632

[22] Filed: Aug. 4, 1989

Related U.S. Application Data

[63] Continuation of Ser. No. 107,199, Oct. 13, 1987, abandoned, which is a continuation-in-part of Ser. No. 912,755, Sep. 26, 1986, abandoned.

[51] Int. Cl.[5] .................. A01H 4/00; C12N 15/05; C12N 15/12
[52] U.S. Cl. .................. 800/205; 435/240.4; 435/172.3; 435/68.1; 435/69.1; 935/30; 935/64; 935/67; 935/35; 536/27
[58] Field of Search .............. 435/172.3, 68, 240, 435/317, 68.1, 240.4, 69.2; 536/27; 800/1, 200, 208; 935/27, 30, 67, 38

[56] References Cited
PUBLICATIONS

Telakowski-Hopkins et al. (1985), J. Biochem. 260:5820-5825, Rat Liver Glutathione S-Transferases.
Zurawski et al. (1982), PNAS 79:7699-7703, Nucleotide Sequence of Gene for the $M_r$ 32,000 Thylakoid . . . .
Comai et al. (1985), Nature 317:741-743, An Altered aroA Gene Product Confers Resistance to the Herbicide Glyphosate.
Hirschberg et al. (1983), Science 222:1346-1349, Molecular Basis of Herbicide Resistance in Amaranthus hybridus.
Pickett et al. (1984), J. Biol. Chem. 259:5182-5186, Rat Liver Glutathione S-Transferases.
Ding et al. (1985), J. Biol. Chem. 260:13268-13271, Rat Liver Glutathione S-Transferases.
Lai et al (1984), J. Biol. Chem. 259:5536-5542, The Nucleotide Sequence of a Rat Liver Glutathione S--Transferase Subunit cDNA Clone.
Taylor et al. (1984), Biochem J. 219:223-231, *Construction and Characterization of a Plasmid Containing Complementary DNA to* . . . .
Mazur et al. (1985), World Biotech. Rep. 2:97-108, Cloning Herbicide Resistance Genes Into and Out of Plants.

*Primary Examiner*—Elizabeth C. Weimar
*Assistant Examiner*—Gary Benzion
*Attorney, Agent, or Firm*—Steven R. Lazar

[57] ABSTRACT

The invention relates to plant cells and dicotyledonous plants transformed with chimeric rat glutathione-S-transferase gene constructs. Transgenic tobacco plants and progeny expressed the chimeric gene constructs under the control of a plant promoter. The transgenic plants and progeny demonstrated resistance to a herbicide which is normally inhibitory to plants not expressing the chimeric construct.

24 Claims, 15 Drawing Sheets

HERBICIDAL TOLERANT PLANTS CONTAINING RAT GLUTATHIONE S-TRANSFERASE GENE

The present invention was made using funds of the U.S. Government. The Government has certain rights in this invention.

This application is a continuation of application Ser. No. 107,199, filed Oct. 13, 1987, now abandoned, which is a continuation-in-part of Ser. No. 912,755, filed Sep. 26, 1986, now abandoned.

FIELD OF THE INVENTION

This invention relates to the use of recombinant DNA technology for the transformation of plants to confer herbicide tolerance to plants by detoxification of the herbicide. More specifically, the invention concerns the construction and use of a recombinant DNA molecule that includes a glutathione S-transferase (GST) gene that upon expression in a plant increases the levels of GST enzymatic activity in the plant.

BACKGROUND OF THE INVENTION

Glutathione S-transferases (EC 2.5.1.1B) are a class of enzymes involved in the detoxification of xenobiotics. These enzymes are ubiquitous to most living organisms, including microorganisms, plants, insects, and animals. Each gluthatione S-transferase (GST) enzyme within this class is distinct; however, the enzymes do exhibit some overlapping substrate specificity. Jakoby et al., "Rat Glutathione S-transferases: Binding and Physical Properties," in *Glutathione Metabolism and function*, edited by I. Arias and W. Jakoby (Raven Press, New York, 1976); Reddy et al., "Purification and Characterization of Individual Glutathione S-Transferase from Sheep Liver," *Archives of Biochem. and Biophys.*, 224:87–101 (1983).

Of the multiple GST functions, GST's catalysis of the conjugation of glutathione to electrophilic compounds is of particular interest. H. Rennenberg, "Glutathione Metabolism and Possible Biological Roles in Higher Plants," *Phytochemistry*, 21:2771–2781 (1982); Meister and Tate, "Glutathione and Related Gamma-Glutamyl Compounds: Biosynthesis and Utilization," in *Ann. Rev. Biochem.*, 45:560–604 (1976). Many xenobiotics, including herbicides, pesticides, and insecticides are electrophilic compounds. In the conjuation of the glutathione and the electrophilic center of the compound, the sulfhydryl group of glutathione reacts with the electrophilic center of the compound. Glutathione participates as a nucleophile by conjugation with the electrophile compound. This conjugation is catalyzed by a specific GST enzyme. (Rennenberg, supra).

In plants, this reaction is important as it provides a mechanism for detoxification of the xenobiotic compound. The conjugated electrophilic, xenobiotic compound is rendered water-soluble and non-toxic to the plant.

It would therefore be desirable to develop plants that are tolerant to herbicides by increasing the levels of glutathione S-transferase enzymatic activity in said plants using genetic engineering techniques. In such a manner, it would be possible to confer herbicide tolerance to a plant.

SUMMARY OF THE INVENTION

This invention is directed to recombinant DNA molecules that confer herbicide tolerance to a plant by producing proteins that detoxify herbicides. Known detoxification mechanisms include the conjugation of glutathione to an electrophilic compound catalyzed by glutathione S-transferase; D-amino acid conjugation to 2,4-dichlorophenoxyacetic acid (2,4-D) and hydroxylation and carbohydrate conjugation of sulfonylurea. More particularly, this invention is directed to herbicide tolerant plants transformed with a recombinant DNA molecule encoding an enzyme that detoxifies herbicides. Specifically, this invention further relates to the recombinant DNA molecules comprising genetic sequences coding for glutathione S-transferase polypeptides and to herbicide tolerant, transformed plant cells with increased levels of glutathione S-transferase enzymatic activity. In this invention, the plant cell is transformed by a glutathione S-transferase (GST) gene, which, upon expression or overexpression, confers herbicide tolerance.

This invention also relates to plants regenerated from the transformed plant cells and the seed thereof as well as to progeny of plants regenerated from the transgenic plant cells, including mutant and variant progeny.

The invention also relates to chimeric genetic constructs containing the glutathione S-transferase gene, cloning vectors and hosts, and methods for conferring herbicide tolerance to plants.

BRIEF DESCRIPTION OF THE DRAWINGS

FIGS. 7*f* and *g* describe the construction of pCIB10a.

DEFINITIONS

Figure 1:
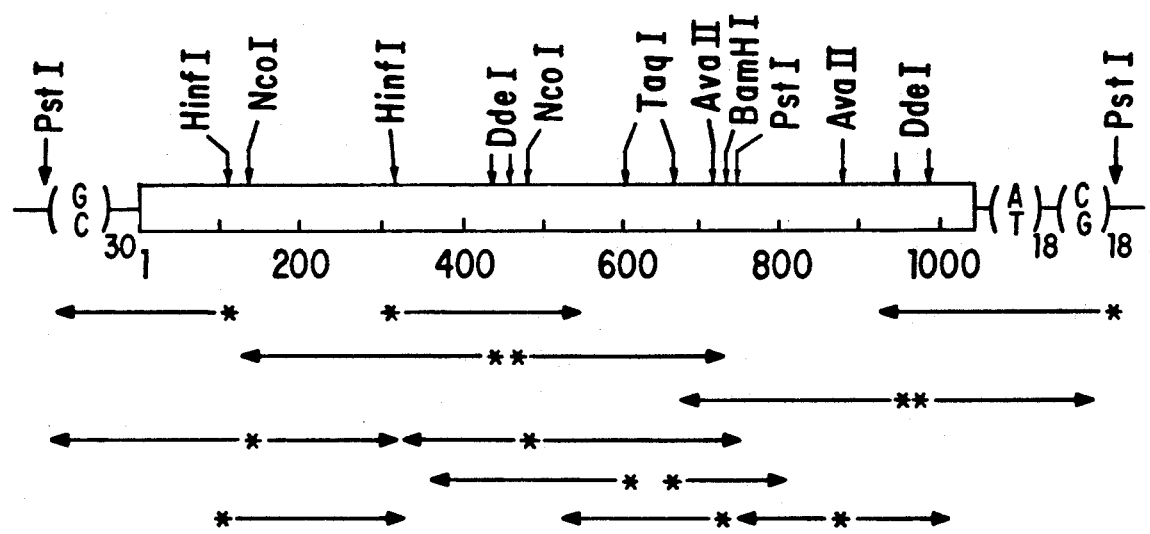
FIG. 1 shows the sequencing strategy for the pGTR200 cDNA insert of $Y_b200$, a rat liver glutathione S-transferase gene.

In the detailed description that follows, a number of terms used in recombinant DNA and plant genetics technology are utilized. In order to provide a clear and consistent understanding of the specification and claims, including the scope to be given such terms, the following definitions are provided:

Heterologous Gene or DNA. A sequence of DNA encoding a specific product, products, or biological function that is obtained from a different species than that species into which the gene is introduced, also called a foreign gene or DNA.

Homologous Gene or DNA. A sequence of DNA encoding a specific product, products or biological function that is obtained from the same species into which the gene is introduced.

Plant Promoter. A DNA expression control sequence that is capable of causing the transcription in a plant of any homologous or heterologous DNA genetic sequence operably linked to such promoter.

Overproducing Plant Promoter (OPP). A plant promoter capable of causing the expression in a transgenic plant cell of any operably linked functional genetic sequence or sequences to levels (measured by mRNA or polypeptide quantities) that are substantially higher than the levels naturally observable in host cells not transformed with said OPP.

Glutathione S-Transferase. The definition of this enzyme is functional, and includes any glutathione S-transferase (GST) capable of functioning in a given desired plant to catalyze the conjugation of glutathione and an electrophilic compound. The term, therefore, includes not only the enzyme from the specific plant species involved in the genetic transformation, but may include GST from other plant species or microbial or mammalian cells, if such GST is capable of functioning in the transgenic plant cells. The term GST includes amino acid sequences longer or shorter than the length of natural GSTs, such as functional hybrid or partial fragments of GSTs, or their analogues.

Plant. Any photosynthetic member of the kingdom Planta that is characterized by a membrane-bound nucleus, genetic material organized into chromosomes, membrane-bound cytoplasmic organelles, and the ability to undergo meiosis.

Plant Cell. The structural and physiological unit of plants, consisting of a protoplast and cell wall.

Plant Tissue. A group of plant cells organized into a structural and functional unit.

Plant Organ. A distinct and visibly differentiated part of a plant such as root, stem, leaf or embryo.

DETAILED DESCRIPTION OF THE INVENTION

Herbicide Tolerant Plants with Increased GST Enzymatic Activity Level

This invention is directed to recombinant DNA molecules that confer herbicide tolerance to a plant by detoxifying herbicides. Known detoxification mechanisms include hydroxylation and carbohydrate conjugation of sulfonylurea (Hutchison, et al., *Pesticide Biochem. and Physiol.*, 22:2430249 (1984)), D-amino acid conjugation to 2,4-D (Davidonis, et al., *Plant Phys.*, 70:357-360 (1982)) and the conjugation of glutathione to an electrophilic compound catalyzed by glutathione S-transferase. More particularly, this invention is directed to herbicide tolerant plants transformed with a recombinant DNA molecule that detoxifies herbicides. Specifically, this invention further relates to recombinant DNA molecules comprising a genetic sequence coding for a glutathione S-transferase polypeptide and to herbicide tolerant, transgenic plant cells and plants with increased levels of glutathione S-transferase enzymatic activity. The glutathione-containing plant cell and plants are tranformed by a glutathione S-transferase (GST) gene that, upon express ion in said plant cell and plant, increases the level of GST enzymatic activity and thus confers herbicide tolerance to the plant. This invention uses genetic engineering techniques in the modification of these plants.

The term "herbicide tolerant plant" as used herein is defined as a plant that survives and preferably grows normally at a usually effective dose of a herbicide. Herbicide tolerance in plants according to the present invention refers to detoxification mechanisms in a plant, although the herbicide binding or target site is still sensitive. Resistance is the maximum tolerance that can be achieved.

Detoxification should be distinguished from another mechanism for conferring herbicide tolerance in which the herbicide binding or target site is changed so that it is no longer sensitive. In the present invention, the herbicide binding site remains sensitive but the herbicide never binds to it because the herbicide is detoxified by, for example, the GST enzyme. Thus, the term "herbicide tolerance" as used herein is meant to include tolerance and resistance to herbicides due to detoxification of the herbicide by, for example, increased GST enzymatic activity levels. The herbicide tolerant plants of the present invention survive without damage in the presence of certain herbicides that are lethal or that damage the growth or vigor of herbicide sensitive plants.

The herbicides that are contemplated in this invention include all those that are capable of being detoxified by, for example, forming conjugates with plant glutathione or analogues or homologues of glutathione, typically any electrophilic compound. Of particular interest in this invention are those herbicides that have chlorine residues. Herbicides that are contemplated in this invention include, but are not limited to, triazines, including chlorotriazines, acetamides including chloroacetanilides, sulfonylureas, imidazolinones, thiocarbamates, chlorinated nitrobenzenes, diphenyl ethers and the like. Some specific examples of herbicides include atrazine, alachlor, S-ethyl dipropylthiocarbamate, and diphenylethyls. See also, *Herbicide Resistance in Plants* (H. LeBaron and J. Gres sel, editors, 1982).

Some of the herbicides are typically potent inhibitors of photosynthesis. Frear et al., *Phytochemistry,* 9:2123-2132 ( 1970) (chlorotriazines); Frear et al., *Pesticide Biochem. and Physiol.,* 20:299-310 (1983) (diphenylether); Lay et al., *Pesticide Biochem. and Physiol.,* 6:442-456 (1976) (thiocarbamates); and Frear et al., *Pesticide Biochem. and Physiol.* 23:56-65 (1985) (metribuzin). Others deactivate enzymes necessary for amino acid biosynthesis.

Although the term "herbicides" is used to describe these compounds, the use of this term herein is not meant to be limiting. For example, many insecticides and pesticides (for controlling diseases, parasites, and predators) that are applied to plants have deleterious effects on plant vigor. The insecticidal or pesticidal agent may be absorbed into the plant tissues either through leaves and stems, or from the soil, through the plant's root system. Moreover, there are many xenobiotics that are electrophilic compounds capable of being conjugated by glutathione and catalyzed by the GST enzymatic activity. These xenobiotic compounds are within the scope of this invention.

In one embodiment of this invention, the herbicides contemplated are sensitizers, that is, inhibitors of the GST enzymatic activity. These sensitizers inhibit the endogenous detoxification mechanism by forming a GST-sensitizer conjugate. The application of an herbicide and a sensitizer, for example, tridiphane, to a plant will inhibit the enzymatic conjugation of glutathione and an herbicide. Ezra et al., "Tridiphane" as a Synergist for Herbicides in Corn (*Zea mays*) and Proso Millet (*Panicum miliaceum*), *Weed Science*, 33:287-290 (1985).

Thus, in this invention, the genetic engineering techniques used to confer GST enzymatic activity, or increased levels of GST enzymatic activity, to a plant results in the transgenic plant being more tolerant or resistant to sensitizers such as tridiphane. In this manner, for instance, a sensitizer and an herbicide in combination can be applied to herbicide sensitive plants and simultaneously to herbicide tolerant plants according to this invention. The combination of sensitizer and herbicide will be typically toxic to the herbicide sensitive plants, but not to the transgenic tolerant plants.

Any plant that contains glutathione or analogues, such as homoglutathione, and that is capable of undergoing genetic manipulation by genetic engineering techniques may be used in this invention. The transgenic plant should also be capable of expressing the GST gene. As used herein, the term "plant" includes plant cells, plant protoplasts, plant tissue culture that can be cultured and induced to form plants, plant calli, plant clumps and plant cells that are intact in plants or parts of plants. "Plant" also refers to pollen that may be transformed by genetic engineering techniques.

Glutathione in plants is typically found in highest concentrations in the subcellular compartments. The highest concentration of glutathione is in the plant plastids, typically in the chloroplasts. (Rennenberg, H., *Phytochemistry,* 21:2771-2781 (1982)). Glutathione has a structure of gamma-L-glutamyl-L-cysteinyl-glycine. A homologous form of glutathione, homoglutathione, has been identified in some plants, with the structure of gamma-L-glutamyl-L-cysteinyl-beta-alanine. (Carnegie, P., *Biochem. J.,* 89:459-471 (1963) and Carnegie, P., *Biochem. J.,* 89:471-478 (1963)). Plants contain varying amounts of glutathione or homoglutathione. For example, several legumes contain mainly homoglutathione, while other legumes contain mainly glutathione. Typically, where either homoglutathione or glutathione is predominant in a plant, only reduced amounts of the other compound is found. (Rennenberq, supra.)

The coding region for the glutathione S-transferase (GST) gene that may be used in this invention may be homologous or heterologous to the plant cell or plant being transformed. It is necessary, however, that the genetic sequence coding for GST be expressed, and produce a functional enzyme or polypeptide in the resulting plant cell. Thus, the invention comprises plants containing either homologous GST genes or heterologous GST genes that express the GST enzyme. Further, the heterologous GST may be from other plant species, or from organisms of different kingdoms, such as microbes or mammals.

As previously described, the GST enzymes are a class of enzymes that are multifunctional. Thus, it is also necessary to choose a GST gene that will catalyze the conjugation of glutathione and an electrophilic compound. Since GST recognizes glutathione as a substrate, it was uncertain prior to this invention whether the GST enzyme specific for glutathione conjugation would accept homoglutathione in transformed plants. Frear et al., *Phytochemistry,* 9:2123-2132 (1970) (indicating that glutathione S-transferase was specific for reduced glutathione). The requisite GST enzyme specific for glutathione can be identified and chosen using an assay that will determine substrate specificity to differentiate the various glutathione S-transferases. In typical assay, the glutathione specific GST can be characterized by affinity chromatography. Tu et al., *Biochem. and Biophys. Research Comm.,* 108:461-467 (1982); Tu et al., *J. Biol. Chem.,* 258:4659-4662 (1983); and Jakoby et al., in *Glutathione; Metabolism and Function,* (Raven Press, New York, 1976).

In one embodiment of this invention, the GST comprises a plant GST that is homologous to the plant to be transformed. In another embodiment of this invention, the GST comprises a plant GST that is heterologous to the plant to be transformed. Plants that contain an abundance of GST include corn and sorqhum. In still another embodiment of this invention, the GST comprises a mammalian GST. Mammalian GSTs are known and are described in Reddy, et al., *Archives of Biochem. and Biophysics,* 224:87-1 01 (1983) (sheep liver); Tu et al., *J. Biol. Chem.,* 258:4659-4662 (1983) (rat tissue including, heart, kidney, liver, lung, spleen, and testis). The preferred GST gene comprises the coding region of a rat liver GST gene, and especially $Y_b200$ described in example IA and the completed $Y_b187$ as described in Example IB. However, other GST genes are known and may be used in this invention.

For example, the N-terminal amino acid sequences of a number of GST proteins from mice and rats have been determined, such as the Rat "X", Rat "A", Mouse Gt-9.3, Mouse GT-8.7, Rat 4-4, Rat 3-3, Rat 1-1 and Rat 1-2 transferases. Mannervik, *Adv. Enzymol. Relat. Areas Mol. Biol.,* 57:357-417 (1985). In addition, the GST proteins from mammals such as Rhesus monkey GST and several human GSTs have been characterized. Mannervik (1985). Using these proteins, the GST gene can be isolated and cloned.

The DNA sequence coding for glutathione S-transferase may be constructed entirely of genomic DNA, or entirely of cDNA. Alternatively, the DNA sequence may be a hybrid construction of both cDNA and genomic DNA, in which case the cDNA may be derived from the same gene as the genomic DNA, or the cDNA and the genomic DNA may be derived from different genes. In either case, both the genomic DNA and/or the cDNA separately may be constructed from the same gene, or from different genes. If the DNA sequence comprises portions from more than one gene, the portions of genes may all come from the same organism; from organisms of more than one strain, variety or species of the same genus; or from organisms of more than one genus of the same or of different kingdoms.

Portions of DNA sequences may be joined together to form the total glutathione S-transferase coding sequence by methods that are known in the art. Some suitable methods include, for example, in vivo recombination of DNA sequences having regions of homology in vitro ligation of appropriate restriction fragments.

There are a variety of embodiments encompassed in the broad concept of the invention. In one of its embodiments, this invention comprises chimeric genetic sequences containing:

(a) a first genetic sequence coding for the glutathione S-transferase polypeptide that, upon expression of the gene in a given plant cell, is functional for glutathione S-transferase activity; and (b) one or more additional genetic sequences operably linked on either side of the GST coding region. These additional genetic sequences contain promoter and/or terminator regions. The plant regulatory sequences may be heterologous or homologous to the host cell.

Any promoter and any terminator capable of inducing expression of a GST coding region may be used in the chimeric genetic sequence. Some suitable examples of promoters and terminators include those from nopaline synthase (nos), octopine synthase (ocs) and cauliflower mosaic virus (CaMV) genes.

One type of efficient plant promoter that may be used is an overproducing plant promoter. Such promoters, in operable linkage with the genetic sequence for GST, should be capable of promoting expression of said GST such that the transformed plant is tolerant to an herbicide due to the presence of, or increased levels of, GST enzymatic activity. Overproducing plant promoters that may be used in this invention include the promoter of the small subunit (ss) of the ribulose-1,5-bisphosphate carboxylase from soybean (Berry-Lowe et al., J. Molecular and App. Gen., 1:483-498 1982)), and the promoter of the chlorophyll a/b binding protein. These two promoters are known to be light induced in eucaryotic plant cells (see, for example, *Genetic Engineering of Plants, an Agricultural Perspective*, A. Cashmore, Plenum, New York 1983, pages 29-38, Coruzzi G. et al., *The Journal of Biological Chemistry*, 258:1399 (1983), and Dunsmu ir, P. et al., *Journal of Molecular and Applied Genetics*, 2:285 (1983)).

The chimeric genetic sequence comprising the glutathione S-transferase gene operably linked to a plant promoter can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells, typically resistance to antibiotics or resistance to selected herbicides. The transforming vectors can be selected by these phenotypic markers after transformation in a host cell.

Host cells that may be used in this invention include procaryotes, including bacterial hosts such as *A. tumefacien s, E. coli, S. typhimurium, Serratia marcenscens* and cyanobacteria. Eucaryotic host cells such as yeast, filamentous fungi, and plant cells may also be used in this invention.

The cloning vector and host cell transformed with the vector are used in this invention typically to increase the copy number of the vector. With an increased copy number, the vectors containing the GST gene can be isolated and, for example, used to introduce the chimeric genetic sequences into the plant cells.

The introduction of DNA into host cells may be accomplished by methods known in the art. Bacterial host cells can be transformed, for example, following treatment of the cells with calcium chloride.

DNA may be inserted into plant cells by contacting protoplasts of the cells directly with the DNA. Alternatively, DNA may be inserted into plant cells by contacting the cells with viruses or with Agrobacterium. Contact with viruses and Agrobacterium may occur through infection of sensitive plant cells or through co-cultivation of protoplasts of plant cells with Agrobacterium. These methods are discussed in greater detail below.

There are a number of methods for the direct insertion of DNA into plant cells. For example, the genetic material contained in the vector can be microinjected directly into plant cells by use of micropipettes to mechanically transfer the recombinant DNA. The genetic material may also be transferred into plant protoplasts following treatment of the protoplasts with polyethylene glycol. (Paszkowski et al., *EMBO J.*, 3:2717-22 (1984)).

In an alternate embodiment of this invention, the GST gene may be introduced into the plant cells by electroporation. (Shillito et al., Biotechnology, 3:1099-1103 (1985)); Fromm et al., *Proc. Nat'l Acad. Sci. USA*, 82:5824 (1985)). In this technique, plant protoplasts are electroporated in the presence of plasmids containing the GST genetic construct. Electrical impulses of high field strength reversibly render biomembranes permeable, allowing the introduction of the plasmids. Electroporated plant protoplasts reform cell walls, divide, and form plant calli. Selection of the transgenic plant cells with the expressed GST enzyme can be accomplished using the phenotypic markers as described above.

Cauliflower mosaic virus (CaMV) may also be used as a vector for introducing the GST gene into plant cells in this invention. (Hohn et al., in "Molecular Biology of Plant Tumors", Academic Press, New York, 1982 pages 549-560; Howell, U.S. Pat. No. 4,407,956). The entire CaMV viral DNA genome is inserted into a parent bacterial plasmid creating a recombinant DNA molecule that can be propagated in bacteria. The recombinant plasmid is cleaved with restriction enzymes either at random or at unique non-vital sites in the viral portion of the recombinant plasmid, for example, at the gene for aphid transmissability, for insertion of the GST genetic sequence. A small oligonucleotide, described as a linker, having a unique restriction site may also be inserted. The modified recombinant plasmid again is cloned and further modified by introduction of the GST genetic sequence thereof into a unique restriction site. The modified viral portion of the recombinant plasmid is then excised from the parent bacterial plasmid, and used to inoculate the plant cells or plants.

Another method of introducing the GST gene into the cells is to infect a plant cell with *Agrobacterium tumefaciens* transformed with the GST gene. Under the appropriate conditions known in the art, the transgenic plant cells are grown to form shoots and roots, and to develop further into plants. The GST genetic sequences can be introduced into appropriate plant cells, for example, by means of the Ti plasmid of *Agrobacterium tumefaciens*. DeCleene et al., Bot. Rev., 47, 147-194 (1981); Bot. Rev., 4 2, 389-466 (1976). The Ti plasmid is transmitted to plant cells on infection by *Agrobacterium tumefaciens* and is stably integrated into the plant genome. Horsch et al., *Science*, 233:496-498 (1984); Fraley et al., *Proc. Nat'l Acad. Sci. USA*, 80:4803 (1983).

For plants whose cells are not sensitive to infection by Agrobacterium, one can resort to co-cultivation of the Agrobacterium with the corresponding protoplast.

Ti plasmids contain two regions essential for the production of transformed cells. One of these, the transfer DNA (T-DNA) region, is transferred to plants and induces tumor formation. The other, the virulent (vir) region, is essential for the formation but not maintenance of tumors. The transfer DNA region can be increased in size by the insertion of the GST genetic sequence without its transferring ability being affected. By removing the tumor-causing genes so that transgenic plant cells are non-tumorous, and adding a selectable marker, the modified Ti plasmid can be used as a vector for the transfer of the gene constructs of the invention into an appropriate plant cell.

The vir region causes the T-DNA region to be transferred from Agrobacterium to the genome of a plant cell irrespective of whether the T-DNA region and the vir region occur on the same vector or on different vectors in the Agrobacterium cell. A vir region on a chromosome also induces transfer of T-DNA from a vector into a plant cell.

The preferred system for transferring a T-DNA region from Agrobacterium into plant cells comprises a vir region on a vector other than the vector containing the T-DNA region. Such a system is known as a binary vector system and the T-DNA-containing vector is known as a binary vector.

Any T-DNA-containing vector that can be transferred into plant cells and that allows the transformed cells to be selected is suitable for use in this invention. A vector constructed from a promoter, a coding sequence and pCIB10 is preferred.

Any vir region-containing vector that causes the transfer of a T-DNA region from Agrobacterium to plant cells may be used in this invention. The preferred vir region-containing vector is pCIB542.

Plant cells or plants transformed with DNA in accordance with this invention can be selected by an appropriate phenotypic marker that is present in the DNA in addition to the GST gene. These phenotypic markers include, but are not limited to, antibiotic resistance markers, such as kanamycin and hygromycin genes, or herbicide resistance markers. Other phenotypic markers are known in the art and may be used in this invention.

All plants whose cells can be transformed by direct insertion of DNA or by contact with Agrobacterium and regenerated into whole plants can be subjected to the methods of this invention so as to produce transgenic whole plants that contain the transferred GST gene. There is an increasing body of evidence that practically all plants can be regenerated from cultured cells or tissues, including but not limited to all major cereal crop species, sugarcane, sugar beet, cotton, fruit and other trees, legumes and vegetables. Limited knowledge presently exists on whether all of these plants can be transformed by Agrobacterium. Even species that are not natural plant hosts for Agrobacterium may be transformable in vitro. For example, monocotyledous plants and, in particular, cereals and grasses are not natural hosts to Agrobacterium. Attempts to transform them using Agrobacterium have been unsuccessful until recently. HooyKaas-Van Slogteren et al., Nature, 311:763-764 (1984). There is growing evidence now that certain monocots can be transformed by Agrobacterium. Using novel experimental approaches that have now become available, cereal and grass species may be transformable.

Plant regeneration from cultural protoplasts is described in Evans, et al., "Protoplast Isolation and Culture," in *Handbook of Plant Cell Culture*, 1:124-176 (MacMillan Publishing Co. New York 1983); M.R. Davey; "Recent Developments in the Culture and Regeneration of Plant Protoplasts," *Protoplasts*, 1983—Lecture Proceedings, pp. 19-29, (Birkhauser, Basel 1983); P.J. Dale, "Protoplast Culture and Plant Regeneration of Cereals and Other Recalcitrant Crops," in *Protoplasts* 1983—Lecture Proceedings, pp. 31-41, (Birkhauser, Basel 1983); and H. Binding, "Regeneration of Plants," in *Plant Protoplasts*, pp. 21-37, (CRC Press, Boca Raton 1985).

Regeneration varies from species to species of plants, but generally a suspension of transformed protoplasts, cells or tissue containing multiple copies of the GST gene is first provided. Embryo formation can then be induced from the suspensions, and allowed to develop to the stage of ripening and germination as natural embryos. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

Some suitable plants for use in this invention include, for example, species from the genera Lotus, Medicago, Onobrychis, Trifolium, Trigonella, Citrus, Linum, Manihot, Daucus, Arabidopsis, Brassica, Raphanus, Sinapsis, Atropa, Capsicum, Datura, Hyoscyamus, Lycopersicon, Nicotiana, Solanum, Petunia, Majorana, Cichorium, Helianthus, Lactuca, Asparagus, Antirrhinum, Panicum, Pennisetum, Ranunculus, Salpiglossis, Glycine, Datura, Gossypium, Malus, Prunus, Rosa, Populus, Allium, Lilium, Narcissus, Anahas, Arachis, Phaseolus, and Pisum.

Since it has been found that Oryza (rice) can be regenerated to whole plants from protoplasts, it should be possible to regenerate other plants belonging to the Gramineae family. Therefore, the following plants may be used in the present invention: Lolium, Zea, Triticum, Sorghum and Bromus.

The preferred plants according to this invention are from the genera Nicotiana spp, (e.g. tobacco), Glycine spp. (especially Glycine max, soybean) and Gossypium spp. (cotton).

The mature plants grown from the transformed plant cells are selfed to produce seeds, some of which contain the gene for the increased GST enzymatic activity level in proportions that follow well established laws of inheritance. These seeds can be grown to produce plants that are herbicide tolerant. The tolerance of these seeds can be determined, for example, by growing the seeds in soil containing an herbicide. Alternatively, the herbicide tolerance of the transformed plants can be determined by applying an herbicide to the plant.

Homozygous lines can be produced by repeated selfing to give herbicide tolerant inbreds. These inbreds can be used to develop herbicide tolerant hybrids. In this method an herbicide tolerant inbred line is crossed with another inbred line to produce an herbicide resistant hybrid.

Parts obtained from the regenerated plant, such as flowers, seeds, leaves, branches, fruit, and the like are covered by the invention provided that these parts comprise the herbicide tolerant cells. Progeny (including hybrid progeny), variants, and mutants of the regenerated plants are also included within the scope of this invention.

Uses For The GST Genetic Constructs and Herbicide Tolerant Plants

The GST genetic constructs, as previously described, may be used in vectors as intermediates in the preparation of herbicide tolerant plant cells, plant organs, plant tissues, and plants.

The importance of herbicide tolerant plants according to the invention is apparent. Such plants would enable farmers to plant an herbicide tolerant crop and then treat the field for weeds without adversely affecting the crop. Further, an herbicide tolerant plant would enable farmers to grow crops in fields that have been treated with herbicides, for example, during a crop rotation cycle in which a naturally tolerant plant is rotated with a naturally sensitive plant. These herbicidally treated fields may contain a certain amount of "herbicide carryover" in the soil. Rotational crops that are naturally sensitive to the herbicide can be injured by such herbicide carryover unless they are rendered tolerant (Sheets, T., *Residue Reviews*, 32:287-3 10 (1970); Burnside, et al., *Weed Science*, 19:290-293 (1971)).

For example, farmers typically plant corn and soybean crops in alternating succession. While the corn crop may naturally be tolerant to certain herbicides, for example certain triazine herbicides such as atrazine, the more sensitive soybean crop, planted after the corn fields have been treated with herbicides, may be damaged. By the use of an herbicide tolerant plant according to this invention, damage due to herbicide carryover is avoided. Fink, et al., *Weed Science*, 17:35-36 (1969) (soybeans); Khan, et al., *Weed Research*, 21:9-12 (1981) (oats and timothy plants); Brinkman, et al., *Crop Science*, 20:185-189 (1980) (oats); Eckert, et al., *J. Range Mgmt.*, 25:219-224 (1972) (wheatgrass).

The invention also encompasses a method of plant control which comprises contacting an herbicide sensitive plant, such as a weed, with plant controlling amounts of an herbicide, wherein the contact is carried out while the sensitive plant is present simultaneously with herbicide tolerant plants of the invention. Thus, foliar herbicidal treatment of plants in a field with both herbicide tolerant plants and herbicide sensitive weeds, and wherein both plant types are simultaneously contacted with the herbicide during the treatment operation, is a method included in the present invention.

Also, as previously described, this invention includes the method of plant control comprising applying an herbicide and a sensitizer simultaneously to both herbicidal tolerant plants and to herbicide sensitive plants.

The term "plant controlling amounts of herbicide" includes, functionally, an amount of herbicide that is capable of affecting the growth or development of a given plant. Thus, the amount may be small enough to simply retard or suppress the growth or development, or the amount may be large enough to irreversibly destroy the sensitive plant.

The actual amount of the herbicide depends on the herbicide and on the plant being controlled. For example, dicotyledonous plants and weeds are often controlled at concentrations of herbicides between 0.5 and 1.5 kg/ha. For monocotyledonous plants, concentrations of herbicides between 0.5 kg/ha and about 2.0 kg/ha are typical. Some herbicides, such as sulfonylurea herbicides, are known to control plants at significantly lower rates.

The herbicide can, of course, be brought into contact with the appropriate plant using well known spraying or spreading methods. For example, foliar administration used in the prior art for control of weeds by atrazine can be used with atrazine-tolerant plants falling within the invention.

Having now generally described this invention, the same will be better understood by reference to specific examples, which are included herein for purposes of illustration only, and are not intended to be limiting unless otherwise specified.

EXAMPLES

The procedures of the following examples may be generally found in Maniatis et al. *Molecular Cloning*, Cold Spring Harbor Laboratory, 1982. Enzymes, unless otherwise noted, can be obtained from New England Biolabs, and are used in accord with the manufacturers recommendations unless otherwise indicated.

Example IA

Isolation of GST cDNA Clone $Y_b200$

Antibodies

Antisera against homogeneous rat hepatic glutathione S-transferases (GSTs) (affinity chromatography fraction) are raised as described (Tu et al., *Nucleic Acids Res.*, 10:5407-5419 (1982)). The I9G fraction is purified from protein A-Sepharose (Pharmacia) column and concentrated by ultrafiltration (Amic on, XM-50 membrane) as described by Kraus and Rosenberg (Kraus & Rosenberg, *Proc. Nat'l Acad. Sci. USA*, 79:4015-4019 (1982)). It is stored in 50% glycerol and 0.2 mg/ml heparin at $-18°$ C.

Isolation of Polysomes

Livers (ca. 26 g) from two male Sprague-Dawley rats (body weight ca 300 g) are homogenized with a Potter-Elvehjem homogenizer in 150 ml (final volume) of 50 mM Tris-HCl, pH 7.5, 25 mM MgC12' 0.25 M sucrose containing bentonite (1 mg/ml), heparin (0.2 mg/ml) and cycloheximide (1 microgram/ml) in several aliquots to a 15% (wt/vol) homogenate. Polysomes are isolated exactly according to published procedures, Kraus & Rosenberg, supra. The yield is 1389 $A_{260}$ units before, and 1208 $A_{260}$ units after, dialysis.

Immobilization of Polysome-Antibody Complexes and Elution of Specific mRNA

1130 $A_{260}$ units of polysomes were recovered for immunoabsorption with anti-GST IgG (7.1 mg). Protein A-Seph arose affinity chromatography and elution of bound RNAs are carried out as described by Kraus & Rosenberg supra. The eluted RNAs are immediately adjusted to 0.5 M NaCl and 0.5% sodium dodecylsulfate and purified further by oligo(dT))-cellulose column (Aviv & Leder, *Proc. Nat'l Acad. Sci. USA*, 69:1408-1412 (1972); Bant le et al., *Anal. Biochem.*, Z2:413-417 (1976)). The purified poly (A+) RNAs are assayed by in vitro translation and immunoprecipitation (Tu et al., *Nucleic Acids Res.*, 10:5407-5419 (1982); Pelham and Jackson, *Eur. J. Biochem.*, 67:247-256 (1976)) before cDNA synthesis. The immunoprecipitated materials are separated on sodium dodecylsulfate-polyacrylamide gels and visualized after fluorography (Laemmli, *Nature*, 22Z:680-684 (1970); Swanstrom and Shenk, *Anal. Biochem.*, 86:184-192 (1978)).

Isolation of GST cDNA Clones cDNA synthesis is performed according to the method of Okayama and Berg (Okayama and Berg, Mol. Cell Biol., 2:161-1 70 (1982)) as modified by Gubler and Hoffman, (Gubler and Hoffman, *Gene*, 25:263-269 (1983)) with minor modifications. Approximately 100-500 ng of poly(A+) RNA from immunoprecipitated polysomes are used for cDNA synthesis. Reverse transcription of the mRNA into cDNA is in 40 microliters containing 50 nM Tris-HCl pH 8.3, 100 mM NaCl, 10 mM $M_{gpk\ Cl2}$, 10 mM DTT, 4 mM sodium pyrophosphate, 1.25 mM of the four dNTPs, 1800 U/ml RNAsin in (Promega Biotec), 100 micrograms/ml oligo-(dT)12-18 (Pharmacia/PL) and 3,000 U/ml of Reverse Transcriptase (Molecular Genetics).

The reaction is incubated 25 minutes at 43° C., then terminated by addition of 2 microliters of 0.5 M EDTA. The reaction is extracted with 1 volume of phenol:chloroform and the aqueous phase back-extracted with one-half volume of chloroform. The organic phase again back-extracted with TE buffer.

To the combined aqueous phases, 1 volume of 4 M ammonium acetate is added and the nucleic acid is precipitated by addition of 2 volumes of ethanol and chilling on dry ice for 20-30 minutes. The solution is then warmed to room temperature for 5 minutes and centrifuged for 15 minutes in an Eppendorf microfuge at 4° C. The resulting pellet is dissolved in 25 microliters of TE buffer. Ammonium acetate (25 microliters of 4M) and 100 microliters of ethanol are added and the nucleic acid precipitated and recovered as before. The pellet is washed with 70% ethanol, dried and dissolved in 20 microliters of water.

Replacement of the mRNA strand of the mRNA:cDNA hybrid is accomplished in 50 microliters containing 20 mM Tris-Cl pH 7.5, 5 mM magnesium chloride, 10 mM ammonium sulfate, 100 mM KCl, 0.15 mM beta-AND, 0.04 mM of the four dNTPs, 20 microliters of the first strand product, 10-20 microCuries $^{32}$P-dATP, 10 U/ml *E. coli* DNA ligase (New England Biolabs), 230 U/ml DNA polymerase (Boehringer Mannheim) and 8.5 U/ml *E. coli* RNAse H (Pharmacia/PL). The reaction is incubated 90 minutes at 12°-14° C., then one hour at room temperature. The double-stranded cDNA is purified by phenol:chloroform extraction and recovered by ethanol precipitation exactly as described for the first strand product. The final dried pellet is dissolved in 20 microliters of water.

Ten microliters of the double-stranded cDNA are tailed with dCTP in a total volume of 20 microliters containing 100 mM potassium cacodylate pH 7.0, 1 mM CoC12' 0.2 mM DTT, 0.1 mM dCTP and 500 U/ml terminal deoxynucleotidyl transferase (Pharmacia/PL). The reaction is incubated 1-2 minutes at 37° C. after which 20 microliters of 4 mM EDTA is added and the enzyme is heat inactivated by incubation at 65° C. for 10 minutes.

PstI-digested, dG-tailed pBR322 (Bethesda Research Labs, Inc.) is added in approximately 1:1 molar ratio to the dC-tailed, double-stranded cDNA (i.e. about 5-10 fold excess by molecular weight of vector over the estimated amount of cDNA). The DNA solution (cDNA+vector) is diluted to give a final total DNA concentration of 0.5-2.0 ng/microliter (0.5 is optimal) in the presence of 10 mM Tris-HCl pH 7.5, 1 mM EDTA and 150 mM NaCl . The mixture is incubated for 5 minutes at 650° C., then the DNA annealed at 55°-58° C. for 90 minutes.

The annealed cDNA:vector is transformed into E. coli strain MM294 using 5 microliters of DNA per 200 microliter aliquot of transformation competent cells (Hanahan *J. Mol. Biol.*, 155:557-580 (1983)); the control transformation frequency is $1-2 \times 10^8$ transformants per microgram of covalently closed circular pBR322 DNA. The transformed cells are plated on LM plates (without magnesium) containing 17 microgram/ml tetracycline (Hanahan, supra). Resulting colonies are tested for ampicillin sensitivity. Those colonies which are tetracycline resistant and ampicillin sensitive (ca. 50%) are picked for further analysis.

Hybrid-Selected in Vitro Translation of pGTR200.

Plasmid DNAs are purified using an alkaline lysis procedure (Birnboim and Doly, *Nucleic Acids Res.*, 7:1513-1523 (1979)) from 354 ampicillin-sensitive transformants and these DNAs digested with PstI to determine cDNA insert sizes. Among them, 134 contain visible cDNA inserts by agarose gel electrophoresis. Those with inserts greater than 800 nucleotides are analyzed further by Southern blot hybridization (Southern, *J. Mol. Biol.*, 98:503-517 (1975)) using Y=(pGTR261) and $Y_c$(pGTR262) as probes (Lai et al., *J. Biol. Chem.*, 259:5536-5542 (1984); Tu et.al., *J. Biol. Chem.*, 259:9434-9439 (1984)).

Twelve clones which do not hybridize to these probes are then characterized further by hybrid-selected in vitro translation (Cleveland et al., *Cell*, 20:95-105 (1980)). One of these negative clones is designated pGTR200. Rat liver poly(A+) RNAs selected by pGTR200 DNA immobilized on activated aminophenylthioether cellulose (APT-paper) are eluted at 75° C. and 100° C. and used to program in vitro translation in the rabbit reticulocyte lysate system. The in vitro translation products are immunoprecipitated by antisera against total rat liver GSTs followed by sodium dodecylsulfate-polyacrylamide gel electrophoresis. The immunoprecipitated product is of Yb mobility; no other class of GST subunits is selected by pGTR 200. Earlier hybrid-selected in vitro translation experiments wit h Y. and Y clones do not reveal any Yb subunit products (Lai et al. supra; Tu et al. supra).

Nucleotide Sequence of pGTR200 cDNA Insert

The DNA sequence of the cDNA in pGTR200 is determined according to the strategy given in FIG. 1 by the chemical method of Maxam and Gilbert (Maxam and Gilbert, *Methods Enzymol.*, 65:499-560 (1980)). The DNA fragments generated by the various restriction endonuclease cleavages were labeled at the 3' ends. Each determination was repeated at least once.

The nucleotide sequence is given below. The single letter code of amino acids is used for the 218 residue open reading frame. Old and Primrose, *Principles of Gene Manipulation*, (1985), Blackwell's Publications, London, p. 346. The poly (A) addition signal, AATAAA is underlined.

```
         10         20         30         40         50         60
CTGAAGCCAAATTGAGAACACCACAGCGCCAGAACCATGCCTATGATACTGGCATACTGG
                                      M  P  M  I  L  G  Y  W 70         80         90        100        110        120
AACGTCCGCGGGCTGACACACCCGATCCGCCTGCTCCTGGAATACACAGACTCAAGCTAT
 N  V  R  G  L  T  M  P  I  R  L  L  E  Y  T  D  S  S  Y 130        140        150        160        170        180
GAGGAGAAGAGATACGCCATGGGCGACGCTCCCGACTATGACAGAAGCCAGTGGCTGAAT
 E  E  K  R  Y  A  N  G  D  A  P  D  Y  D  R  S  Q  W  L  N 190        200        210        220        230        240
GAGAAGTTCAAACTGGGCCTGGACTTCCCCAATCTGCCCTACTTAATTGATGGATCGCGG
 E  K  F  K  L  G  L  D  F  P  N  L  P  Y  L  I  D  G  S  R 250        260        270        280        290        300
AAGATTACCCAGAGCAATCCCATAATGCGCTACCTTGCCCGCAAGCACCACCTGTGTGGA
 K  I  T  Q  S  N  A  I  N  R  Y  L  A  R  K  N  N  L  C  G 310        320        330        340        350        360
GAGACAGAGGAGGAGCGCATTCGTGCAGACATTGTGGAGAACCACGTCATGGACAACCGC
 E  T  E  E  E  R  I  R  A  D  I  V  E  N  Q  V  N  D  N  R 370        380        390        400        410        420
ATGCAGCTCATCATGCTTTGTTACAACCCCGACTTTGAGAAGCAGAAGCCAGAGTTCTTG
 N  Q  L  I  N  L  C  Y  N  P  D  F  E  K  Q  K  P  E  F  L 430        440        450        460        470        480
AAGACCATCCCTGAGAAGATGAAGCTCTACTCTGAGTTCCTGGGCAAGCGACCATGGTTT
 K  T  I  P  E  K  N  K  L  Y  S  E  F  L  G  K  R  P  W  F 490        500        510        520        530        540
GCAGGGGACAAGGTCACCTATGTGGATTTCCTTGCTTATGACATTCTTGACCAGTACCAC
 A  G  D  K  V  T  Y  V  D  F  L  A  Y  D  I  L  D  Q  Y  N 550        560        570        580        590        600
ATTTTTGAGCCCAAGTGCCTCCACGCCTTCCCAAACCTGAAGGACTTCCTGGCCGGCTTC
 I  F  E  P  K  C  L  D  A  F  P  N  L  K  D  F  L  A  R  F 610        620        630        640        650        660
GAGGGCCTGAAGAAGATCTCTGCCTACATGAAGAGCAGCCGCTACCTCTCAACACCTATA
 E  G  L  K  K  I  S  A  Y  N  K  S  S  R  Y  L  S  T  P  I 670        680        690        700        710        720
TTTTCGAAGTTGGCCCAATGGAGTAACAAGTAGGCCCTTGCTACACTGGCACTCACAGAG
 F  S  K  L  A  Q  W  S  N  K  *

730        740        750        760        770        780
AGGACGTGTCCACATTGGATCCTGCAGGCACCCTGGCCTTCTGCACTGTGGTTCTCTCTC 790        800        810        820        830        840
CTTCCTGCTCCCTTCTCCAGCTTTCTCAGCCCCATCTCCTCAACCTCACCCCAGTCATGC 850        860        870        880        890        900
CCACATAGTCTTCATTCTCCCCACTTTCTTTCATAGTGGTCCCCTTCTTTATTGACACCT 910        920        930        940        950        960
TAACACAACCTCACAGTCCTTTTCTGTGATTTGAGGTCTGCCCTGAACTCAGTCTCCCTA 970        980        990       1000       1010       1020
GACTTACCCCAAATGTAACACTGTCTCAGTGCCAGCCTGTTCCTGGTGGGGGACCTGCCC 1030       1040       1050       1060       1070
CAGGCCTGTCTCATCTTTAATAAAGCCTGAAACACAAAAAAAAAAAAAAAAAA
```

Example IB

Isolation of Partial GST cDNA Clone Y$_b$187

By essentially the same procedure, cDNA clone Y$_b$187 was obtained. Y$_b$187 is a partial cDNA clone lacking 96 nucleotides at the 5' end of the coding sequence. The nucleotide and the corresponding amino acid sequences for the missing 96 nucleotides and Y$_b$187 are given below:

```
      1  0                           30
atg  cct  atg  aca  ctg  ggt  tac  tgg  gac  atc  cgt  ggg  ctg  gct  cac
Met  Pro  Met  Thr  Leu  Gly  Tyr  Trp  Asp  Ile  Arg  Gly  Leu  Ala  His 50                              7 0                          90
gcc  att  cgc  ctg  ttc  ctg  gag  tat  aca  gac  aca  agc  tat  gag  gac
Ala  Ile  Arg  Leu  Phe  Leu  Glu  Tyr  Thr  Asp  Thr  Ser  Tyr  Glu  Asp
```

```
                1 10                                    13 0
aag aag tac agc atg ggg gat gct ccc gac tat gac aga agc cag
Lys Lys Tyr Ser Met Gly Asp Ala Pro Asp Tyr Asp Arg Ser Gln 150                         1 70
tgg ctg agt gag aag ttc aaa ctg ggc ctg gac ttc ccc aat ctg
Trp Leu Ser Glu Lys Phe Lys Leu Gly Leu Asp Phe Pro Asn Leu 19 0                        210
ccc tac tta att gat ggg tca cac aag atc acc cag agc aat gcc
Pro Tyr Leu Ile Asp Gly Ser His Lys Ile Thr Gln Ser Asn Ala 2 30                        25 0                        270
atc ctg cgc tac ctt ggc cgg aag cac aac ctt tgt ggg gag aca
Ile Leu Arg Tyr Leu Gly Arg Lys His Asn Leu Cys Gly Glu Thr 2 90                        31 0
gag gag gag agg att cgt gtg gac gtt ttg gag aac cag gct atg
Glu Glu Glu Arg Ile Arg Val Asp Val Leu Glu Asn Gln Ala Met 330                     3 50
gac acc cgc cta cag ttg gcc atg gtc tgc tac agc cct gac ttt
Asp Thr Arg Leu Gln Leu Ala Met Val Cys Tyr Ser Pro Asp Phe 37 0                         390
gag aga aag aag cca gag tac tta gag ggt ctc cct gag aag atg
Glu Arg Lys Lys Pro Glu Tyr Leu Glu Gly Leu Pro Glu Lys Met 4 10                        43 0                        450
aag ctt tac tcc gaa ttc ctg ggc aag cag cca tgg ttt gca ggg
Lys Leu Tyr Ser Glu Phe Leu Gly Lys Gln Pro Trp Phe Ala Gly 4 70                        49 0
aac aag att acg tat gtg gat ttt ctt gtt tac gat gtc ctt gat
Asn Lys Ile Thr Tyr Val Asp Phe Leu Val Tyr Asp Val Leu Asp 510                         5 30
caa cac cgt ata ttt gaa ccc aag tgc ctg gac gcc ttc cca aac
Gln His Arg Ile Phe Glu Pro Lys Cys Leu Asp Ala Phe Pro Asn 55 0                         570
ctg aag gac ttc gtg gct cgg ttt gag ggc ctg aag aag ata tct
Leu Lys Asp Phe Val Ala Arg Phe Glu Gly Leu Lys Lys Ile Ser 5 90                        61 0                        630
gac tac atg aag agc ggc cgc ttc ctc tcc aag cca atc ttt gac
Asp Tyr Met Lys Ser Gly Arg Phe Leu Ser Lys Pro Ile Phe Ala 6 50
aag atg gcc ttt tgg aac cca aag tag
Lys Met Ala Phe Trp Asn Pro Lys End
```

Example IC

Entire Clone Corresponding to Y$_b$187

Figure 4A:
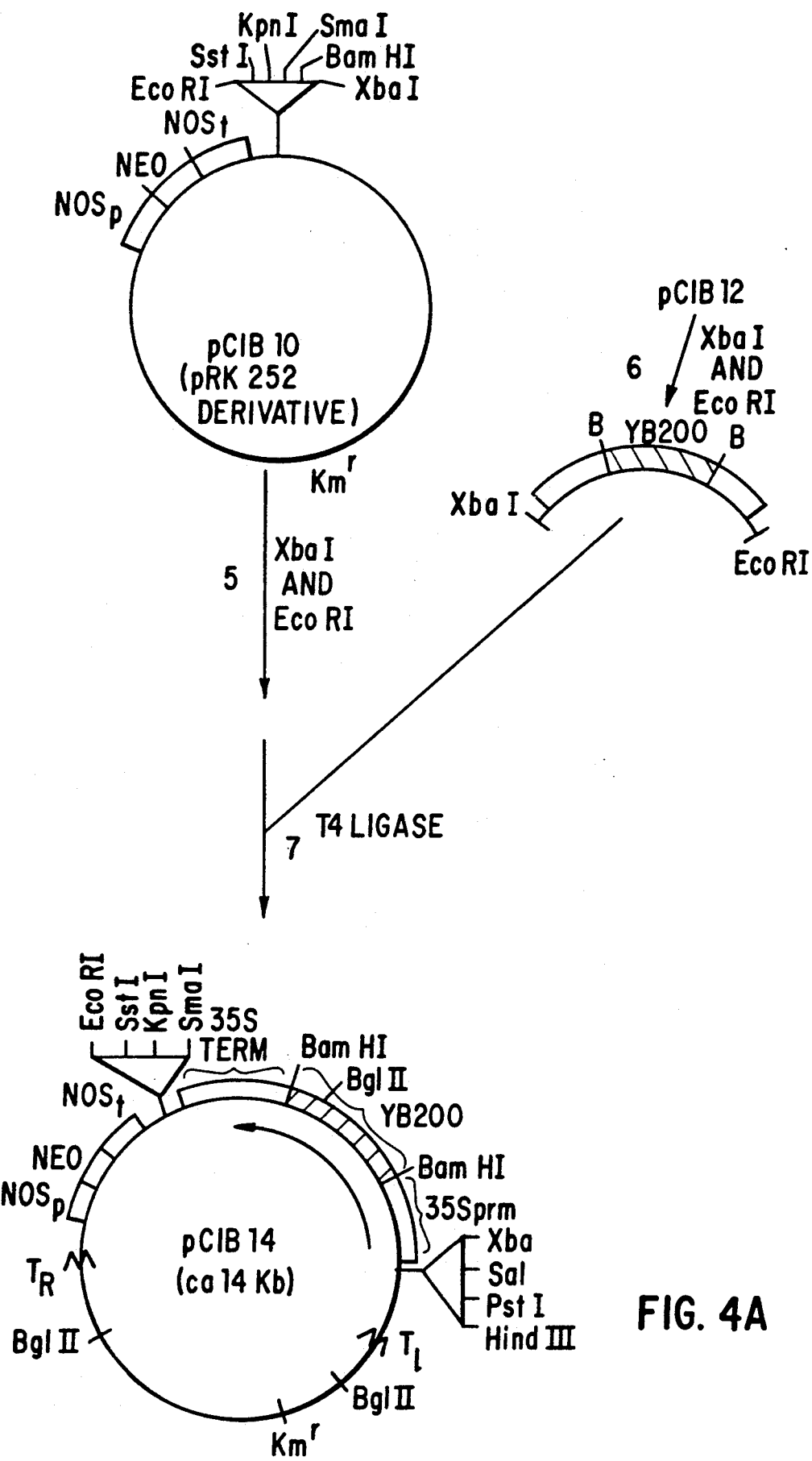
FIG. 4A shows the construction of plasmid pCIB14, a broad host range replicon, containing two chimeric genes inside a T-DNA border, with the chimeric gene with the CaMV 35S promoter linked with the rat liver glutathione S-transferase gene, $Y_b200$, the CaMV terminator and the kanamycin resistant gene, nos-neo-nos.
Figure 4B:
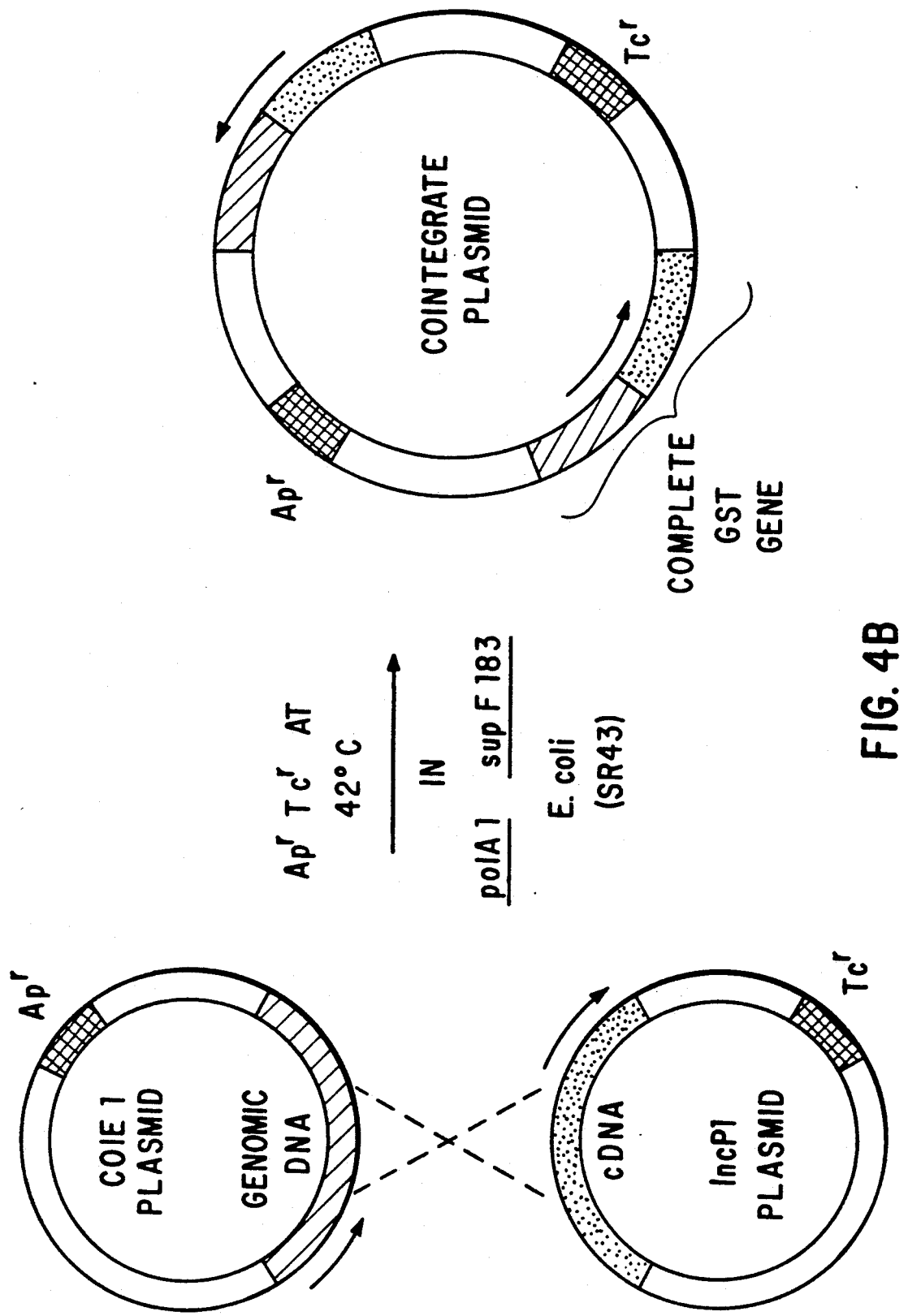
FIG. 4B shows the completion of a partial clone by the in vivo recombination method.
Figure 4C:
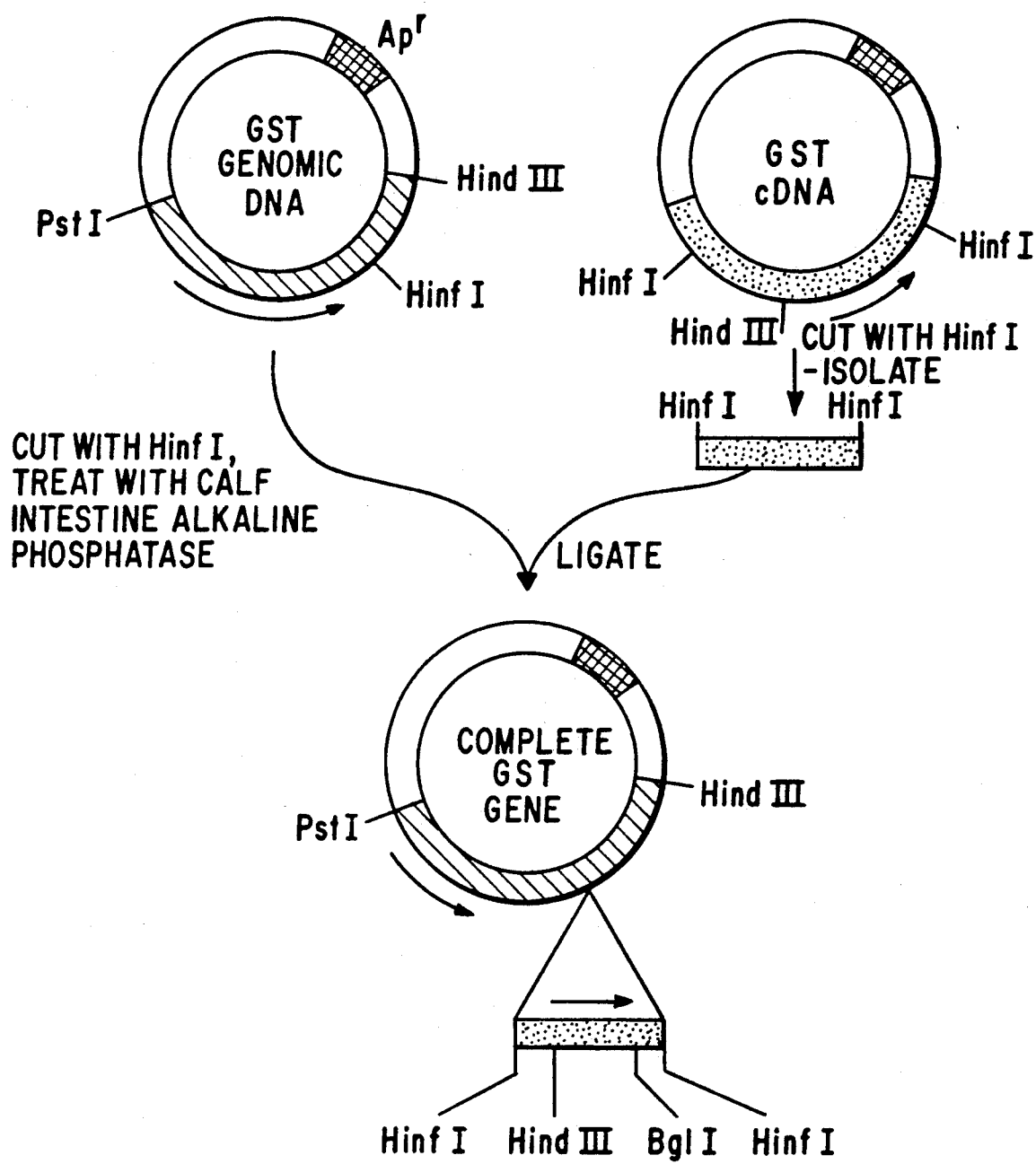
FIG. 4C shows the completion of a partial clone by the in vitro ligation method.

The missing nucleotides are added to Y$_b$187 either in vivo by recombination or in vitro by ligating appropriate restriction fragments. These methods are illustrated in FIGS. 4B and 4C, respectively.

Recombination can be effected by introducing into *E. coli* strain SR43 (ATCC accession number 67217 deposited Sep. 22, 1986) the genomic DNA clone carried on a colE1 plasmid (e.g. pUC8 or pBR322) and the cDNA clone carried on an inc P1 plasmid ( e.g. pRK290). Strain SR34 bears polA1 supF183 mutations (Tacon, W. & Sherratt, D., *Mol. Gen. Genet.*, 147:331–335 (1976)) such that replication of colE1 plasmids is prohibited at the restrictive temperature (42 degrees). Shifting of the SR43 bacteria containing the two plasmids from permissive temperature (28 degrees) to 42 degrees with maintenance of the selection for the antibiotic resistance carried by the colE1 plasmid (e.g. Ap resistance of pBR322) allows selection of bacteria containing cointegrated forms of the two plasmids. Such cointegrate plasmids are formed by recombination at regions of DNA homology. Isolation of cointegrate plasmids allows cloning of the full length cDNA sequence and upstream genomic DNA as a single PstI or BamHI fragment. Ba131 resection of upstream DNA followed by BamHI linker addition allows isolation of a clone containing the full length coding region (confirmed by DNA sequence analysis). The full length coding region is cloned as a BamHI fragment into pCIB710 as described in Example IA for transfer to plant cells. This same fragment is cloned into pDR540 as described in Example IV below for expression in *E. coli.*

Alternatively, the entire clone corresponding to Y$_b$187 can be constructed by ligating appropriate restriction fragments of cDNA and genomic clones together (FIG. 1). Plasmids pUC19 containing the 5' end of the genomic clone inserted as a PstI-HindIII fragment contains approximately the first 400 bases of the coding sequence. The 3' end of the cDNA coding sequence can be isolated as a 630 base HinfI fragment from the partial cDNA clone in BR325. The pUC plasmid cut at its unique HinfI site and the HinfI fragment containing the 3' end of the gene are ligated together, recreating the complete coding sequence of the GST gene. The complete gene is isolated as a B91I-PstI fragment. Bal31 resection of upstream DNA followed by BamHI linker addition allows isolation of the full length coding region without upstream sequences. This BamHI fragment is inserted into pCIB710 and into pDR540 as described above.

Example ID

Hybrid Clones

Hybrid clones derived from coding sequences for different genes are constructed in essentially the same manner as described above for combining the partial cDNA clone $Y_b187$ and the missing nucleotides (Example IC) using heterologous genes as the sources of the two DNA fragments.

Example IE

A cDNA library in lambda gt11 is constructed from poly(A) RNA isolated from rat brains. The cDNA is isolated by antibody screening procedures using antibodies raised against rat brain GST. The isolation of RNA and the construction and isolation of the corresponding cDNA are accomplished by methods described in the prior art, such as those in Young and Davis, Science, 222, 778–782 (1983).

The sequence of the resulting cDNA, which is referred to as $Y_bG1$, is:

```
         10
agacccccagcacc 30                    50
atg ccc atg aca ctg ggt tac tgg gac atc cgt ggg cta gcg cat
Met Pro Met Thr Leu Gly Tyr Trp Asp Ile Arg Gly Leu Ala His 70                    90
gcc atc cgc ctg ctc ctg gaa tac aca gac tcg agc tat gag gag
Ala Ile Arg Leu Leu Leu Glu Tyr Thr Asp Ser Ser Tyr Glu Glu 110                   130
aag aga tac acc atg gga gac gct ccc gac ttt gac aga agc
Lys Arg Tyr Thr Met Gly Asp Ala Pro Asp Phe Asp Arg Ser 150              170                  190
cag tgg ctg aat gag aag ttc aaa ctg ggc ctg gac ttc ccc aat
Gln Trp Leu Asn Glu Lys Phe Lys Leu Gly Leu Asp Phe Pro Asn 210                   230
ctg ccc tac tta att gat gga tca cac aag atc acc cag agc aat
Leu Pro Tyr Leu Ile Asp Gly Ser His Lys Ile Thr Gln Ser Asn 250                   270
gcc atc ctg cgc tat ctt ggc cgc aag cac aac ctg tgt ggg gag
Ala Ile Leu Arg Tyr Leu Gly Arg Lys His Asn Leu Cys Gly Glu 290                   310
aca gaa gag gag agg att cgt gtg gac att ctg gag aat cag ctc
Thr Glu Glu Glu Arg Ile Arg Val Asp Ile Leu Glu Asn Gln Leu 330                   350
atg gac aac cgc atg gtg ctg gcg aga ctt tgc tat aac cct
Met Asp Asn Arg Met Val Leu Ala Arg Leu Cys Tyr Asn Pro 370              390                    410
gac ttt gag aag ctg aag cca ggg tac ctg gag caa ctg cct gga
Asp Phe Glu Lys Leu Lys Pro Gly Tyr Leu Glu Gln Leu Pro Gly 430                   450
atg atg cgg ctt tac tcc gag ttc ctg ggc aag cgg cca tgg ttt
Met Met Arg Leu Tyr Ser Glu Phe Leu Gly Lys Arg Pro Trp Phe 470                   490
gca ggg gac aag atc acc ttt gtg gat ttc att gct tac gat gtt
Ala Gly Asp Lys Ile Thr Phe Val Asp Phe Ile Ala Tyr Asp Val
```

-continued
```
         510                   530
ctt gag agg aac caa gtg ttt gag gcc acg tgc ctg gac gcg ttc
Leu Glu Arg Asn Gln Val Phe Glu Ala Thr Cys Leu Asp Ala Phe 550              570                    590
cca aac ctg aag gat ttc ata gcg cgc ttt gag ggc ctg aag aag
Pro Asn Leu Lys Asp Phe Ile Ala Arg Phe Glu Gly Leu Lys Lys 610                   630
atc tcc gac tac atg aag tcc agc cgc ttc ctc cca aga cct ctg
Ile Ser Asp Tyr Met Lys Ser Ser Arg Phe Leu Pro Arg Pro Leu 650                   670
ttc aca aag atg gct att tgg ggc agc aag tag
Phe Thr Lys Met Ala Ile Trp Gly Ser Lys End 690              710                  730
gaccctgacaggtgggctttaggagaaagataccaaatctcctgggtttgccaagagcccta 750                   770                   790
aggagcgggcaggattcctgagcccccagagccatgttttcttccttccttccattccagtcccca 810                   830                   850
agccttaccagctctcatttttggtcatcaaattcctgccaaacacaggctcttaaaagccct 870                   890                   910
agcaactcctttccattagcaaaatagccttctaaagttaaagtgccccgcccccacccctcg 930                   950                   970
agctcatgtgattggatagttggctcccaacatgtgattattttgggcaggtcaggctccc 990                   1010                  1030
cggcagatggggtctatctggagacagtagattgctagcagctttgaccaccgtagcca 1050                  1070                  1090
agcccctcttcttgctgtttcccgagactagctatgagcaaggtgtgctgtgtcccccagc 1110                  1130                  1150                  1170
acttgtcactgcctctgtaacccgctcctaccgctctttcttcctgctgctgtgagctgtacctcct 1190                  1210
gaccacaaaccagaataaatcattctcccctttaaaaaaaaaaaaaaaaaaaaaa
```

Eample II

Construction of Plasmid pCIB710

The plasmid pLW111, ATCC No. 40235, consists of the three smaller EcoRI fragments of the BJI strain of Cauliflower Mosaic virus (CaMV) (Franck et al., *Cell*, 21:285–294 (1980)) cloned into pMB9. pLW111 is digested with BglII and a 1149 bp fragment (base pairs #6494–7643) isolated. This fragment is ligated into the BamHI site of pUC 19. This restriction fragment codes for both the promoter for the CaMV 35S RNA and the polyA addition signal (i.e. the terminator) for that transcript.

In Vitro Mutagenesis

A unique BamHI site is inserted between this promoter and terminator via in vitro mutagenesis. A 36-base oligonucleotide is synthesized which is identical to the CaMV sequence in that region except that a BamHI restriction site is inserted at base pair #7464 in the sequence.

The 1149 bp BglII fragment from above is cloned into M13mp19 and single-stranded phage DNA isolated. This single-stranded DNA is annealed with the synthetic oligonucleotide, a new strand is synthesized using the oligonucleotide as a primer; and the DNA transfected into *E. coli* strain JM101 (Zoller & Smith, *DNA* 3:479–488 (1980)). M13 phage having the BamHI site inserted are isolated as described in Zoller & Smith, supra.

Selection of Desired Mutant Phage

The 36-base oligonucleotide is labeled by kinasing with $32_p$-ATP. A set of the transfected M13 phage plaques is localized on a nitrocellulose filter. This filter is hybridized with the labelled 36-mer. The filter is washed at increasing temperatures. The labeled 36-mer bound to mutated phase is stable at higher wash temperature. One of these phages stable at higher temperature is isolated and sequenced to confirm the presence of the BamHI site.

Construction of pCIB710

Figure 2:
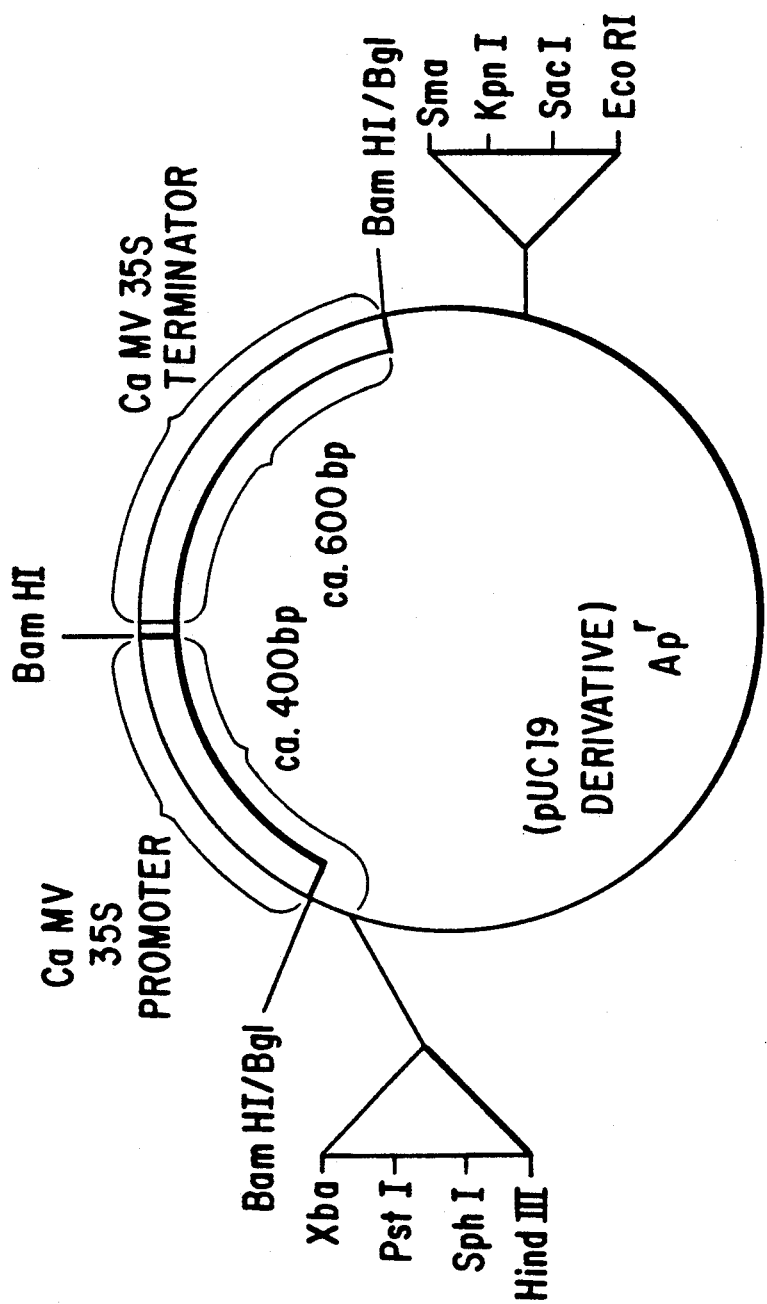
FIG. 2 depicts plasmid pCIB710, an *E. coli* replicon, which includes the promoter for the CaMV 35S DNA transcript and it terminator and polyA addition signal.

Double-stranded DNA isolated from this phage is digested with HindIII and EcoRI. pUC19 is cleaved with HindIII and EcoRI. These two digested DNA's are ligated. Transformants are selected by ampicillin resistance. One transformant from this ligation is pCIB710. This plasmid is shown in FIG. 2.

Example III

Construction of Plasmids pCIB11, pCIB12, pCIB13 and pCIB14

1. The plasmid pGTR200 is digested with HaeII, Psti and Pvu II and the 678 bp HaeII/PstI fragment containing the GST coding sequence is isolated from an agarose gel.

2. This HaeII/PstI fragment is rendered blunt-ended by treatment with T4 DNA polymerase, and BamHI linkers (dCGGATCCG-New England Biolabs) are ligated on to the blunt ends using T4 DNA ligase.

3. The plasmid pCIB710 is cut with BamHl and treated with calf intestinal alkaline phosphatase (Boehringer Mannheim).

4. The BamHl-linkered GST fragment from above is ligated in to BamHl-digested pCIB710, the ligation mixture transformed into E. coli strain HB101 and the desired transformants selected by resistance to ampicillin. Transformants bearing the GST coding sequences in the appropriate orientation for transcription from the CaMV promoter (pCIB12) as well as in the opposite orientation (pCIB11) are characterized.

5. The plasmid pCIB10 (see Example IV) is digested with XbaI and EcoRI.

6. The plasmid pCIB12 is digested with XbaI and gcoRI and the smaller fragment isolated from an agarose gel.

Figure 3:
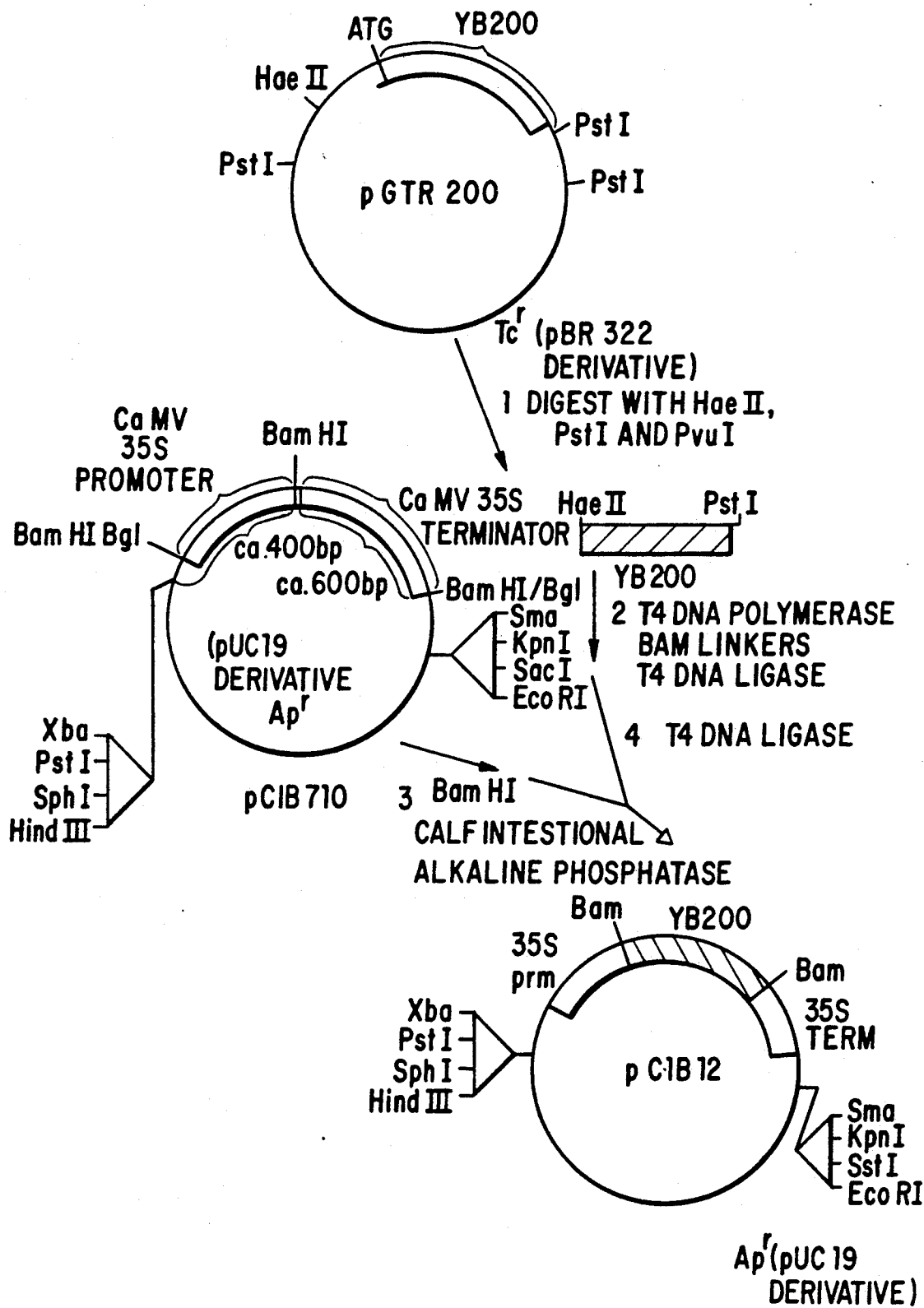
FIG. 3 shows the construction of plasmid pCIB12, an *E. coli* replicon, containing the chimeric gene with the CaMV 35S promoter linked to the rat liver glutathione S-transferase cDNA gene, $Y_b200$, and the CaMV terminator.

7. The isolated XbaI/EcoRI fragment, which bears the chimeric gene, is ligated into the digested pCIB10, the ligation transformed into E. coli HB 101 and transformants selected by kanamycin resistance. These transformants, which bear the GST coding sequence in the appropriate orientation for transcription from the CaMV promoter, are designated pCIB14 (see FIG. 3).

8. The plasmid pCIB11 is similarly manipulated to construct pCIB13, a plasmid having the GST coding sequence in an orientation opposite that appropriate for transcription from the CaMV promoter.

Introduction of pCIB13 and pCIB14 into Agrobacterium

Purified plasmid DNA of pCIB13 or pCIB14 was introduced by transformation into *Agrobacterium tumefaciens* A136 (Watson et al., *J. Bacteriol.*, 123:255-264 (1975)) bearing pCIB542 (see Example VII below). Tranformants were selected on kanamycin (50 ug/ml) and spectinomycin (25 ug/ml).

Example IV

Insertion of $Y_b200$ GST Gene in trp-lac (tac) Expression Vector

The plasmid pCIB12 was digested with BamHI and the 708 bp Bam-linkered GST gene fragment isolated. The plasmid pDR 540 (Pharmacia P-L Biochemicals), a tac expression vector (Russell, D.R. and Bennett, G.N., *Gene*, 20:231-243 (1982)) was digested with BamHI and the GST fragment ligated in. The resulting recombinant plasmid was transformed into E. coli strain JM10 3. Cultures of the resulting strain were induced at the desired time by addition of 1.0 mM isopropyl beta-D-thiogalactoside (IPTG ).

After induction with IPTG and expression of the GST $Y_b200$ gene, the bacterial host cells are pelleted. The pellets formed are resuspended in 59 ml 0.2 M Tris HCl, pH 8.0, and 1 mM EDTA. To this suspension 0.5 ml 100 mM phenylmethylsulfonylfluoride (PMSF) in ethanol and 5 ml 10 mg/ml lysozyme in buffer was added. The suspension was incubated for approximately 15 minutes at 37° C. until the bacterial cells were lysed. The lysed bacterial cell suspension was pelleted and the supernatent collected. The supernatant was dialyzed against 25 nM Tris HCl, pH 8.0 with 1/100 volume of PMSF.

The dialyzed supernatant was assayed for GST enzymatic activity. Following this, the dialyzed supernatant was loaded onto the S-hexylglutathione-agarose affinity column at a flow rate of 0.5 ml/minute. The column was washed with 25 mM Tris HCl, 0.2 M KCl until the absorbance at 280 nm was less than 0.005. After all unbound material had been washed from the column the bound material was eluted with 25 mM Tris HCl, 0. 2 M KCl (pH 8.0) containing 5 mM S-hexylglutathione, and 2.5 mM glutathione. Eluted fractions were monitored at an absorbance of 280 nm. Those fractions which were believed to contain the purified enzyme were individually dialyzed against 0.1 M NaP 04 (pH 6.5) containing PEG to concentrate the fractions, and the n in the same buffer without PEG.

The volumes in each of the dialyzed fractions were recorded for each fraction, the degree of concentration and amount of sample was calculated and then diluted such that the same proportion relative to the starting fraction was present in each fraction. Each fraction was assayed for enzymatic activity.

GST activity was assayed using 1-chloro-2,4-dinitrobenzene (ClDNB) as a substrate. For each reaction, 1 mM ClDNB (20.2 mg/ml in ethanol) was added to 5 mM reduced glutathione (30.8 mg/ml in buffer, 0.1M sodium phosphate, pH 6.5) and GST enzyme. ClDNB and reduced glutathione were prepared fresh daily. The reaction had a final total volume of 1 ml. The reaction was run at room temperature and initiated by the addition of ClDNB. The reaction was monitored on Gilford spectrophotometer at 340 n m. A typical reaction contained 10 to 50 units of GST, where 1 unit is equivalent to 1 nanomole substrate converted per minute per ml.

The protein concentration of the enzymatically active fractions was determined in the starting material (Biorad, BSA standard). Each of the enzymatically active fractions was analyzed on a 15 percent Laemmli gel using dilutions of standard enzyme (1.0 ug, 0.3 ug, and 0.1 ug) as quantitative standards. Purified enzyme was detected by immunoblotting using specific antibody.

Example V

Construction of pCIB10

The construction of plasmid pCIB10 was described in commonly assigned pending application, Ser. No. 757,098 filed July 19, 1985 entitled "Transformation of Plastids and Mitochondria", and incorporated herein by reference. The following steps described and numbered as follows in the above-referenced patent application were used to construct this plasmid.

15. A T-DNA fragment containing the left border from pTiT37 is isolated from pBR325 (EcoRI29) (Yadav et al., *Proc. Nat'l Acad. Sci. USA*, 79:6322 (1982)). pBR325 (?coRI29) is cut with EcoRI and the 1.1 kb fragment linkered with HindIII linkers (New England Biolabs).

16. The plasmid pBR322 (Bolivar et al., *Gene*, 2:75) is cut with HindIII.

17. The left-border containing fragment described in step 15 is ligated into the HindIII digest of pBR322.

18. The left-border containing pBR322 plasmid of step 17 is digested with ClaI and HindIII and the 1.1 kb HindIII/ClaI fragment isolated (Hepburn et al., *J. Mol. Appl. Genet.*, 2:211 (1983)).

19. The plasmid pUC18 (Norrander et al., *Gene*, 26:101 (1983) is cut with HindIII and EcoRI; the 60 bp polylinker is end-labeled using T4 polynucleotide kinase and gamma $^{32}$P-dATP and isolated from an acrylamide gel.

20. The plasmid pBR322 is cut with EcoRI and ClaI and the large fragment isolated.

21. The 60 bp HindIII/EcoRI polylinker and the 1.1 kb HindIII/ClaI fragment of EcoRI 29 is ligated into pBR322 cut with ClaI and EcoRI, constructing pCIB5.

22. A chimeric gene confwrring kanamycin resistance (nos-neo-nos) is taken from Bin 6 (Bevan, *Nucleic Acids Res.*, 12:8711 (1984)) as a SalI/EcoRI fragment.

23. The plasmid pUC18 is cut with EcoRI and SalI.

24. The SalI/EcoRI fragment containing the chimeric gene from step 22 is ligated into the pUC18 cut with EcoRI and SalI.

25. The BamHI recognition site in the termination sequence of this chimeric gene is destroyed by cutting with BamHI, filling in using T4 DNA polymerase, and ligating.

26. The resulting plasmid is cut with SstII (Bethesda Research Laboratories) and HindIII.

27. A fragment containing the 5' part of the nos promoter and the right border of pTiT37 is isolated by cutting pBR325 (Hind23) with HindIII and SstII and isolating the 1.0 kb fragment.

28. This 1.0 kb HindIII/SstII fragment is ligated into the restricted pUC18 of step 26, constructing pCIB4.

29. pCIB5, containing the left T-DNA border, is cut with Aat II, rendered blunt-ended by treatment using T4 DNA polymerase, and then cut with EcoRI.

30. pCIB4 is cut with HindIII, rendered blunt by treatment using Klenow fragment of *E. coli* DNA polymerase and cut with EcoRI.

31. The restricted pCIB5 of step 29 is ligated with the restricted pCIB4 (step 30), constructing pCIB2, a colE1 replicon containing left and right T-DNA borders flanking a chimeric kanamycin-resistance gene and a polylinker.

32. The plasmid pRZ102 (Jorgensen et al., *Mol. Gen. Genet.*, 177:65 (1979)) is digested with BamHI and filled in using Klenow.

33. An AluI partial digest of plamid pA03 (Oka, *J. Mol. Biol.*, 174:217 (1981)) is made.

34. The AluI digest is ligated into the restricted pRZ102 of step 32 above, selecting the desired transformants by resistance to kanamycin.

35. The resulting plasmid has the coding sequence of Tn903 present on a 1.05 kb BamHI fragment which is isolated after BamHI digestion. This fragment is treated with Klenow DNA polymerase.

36. The plasmid pRK252, a derivative of the broad host range plasmid RK2, is available from Dr. Don Helinski of the University of California, San Diego. This plasmid lacks the BglII site present in the parent plasmid pRK290 (Ditta et al., *Proc. Nat'l Acad. Sci. USA*, 77:7347 (1980)). pRK252 is digested with SmaI and SalI, filled in using Klenow, and the large fragment resulting from this digest isolated.

37. The Tn 903-containing fragment, isolated in step 35, is ligated into the large fragment from pRK252, constructing pRK252Km.

38. The plasmid pRK252Km is cut with EcoRI, blunt-ended using Klenow, and linkered with BglII linkers (New England Biolabs).

39. The plasmid pCIB2 is cut with EcoRV and the smaller fragment, containing the right border and the nos-neo-nos, isolated. This fragment is filled-in using Klenow polymerase and linkered with BglII linkers (New England Biolabs).

40. The BglII fragment resulting from step 39 is ligated with the linkered pRK252KM of step 38, producing pCIB10.

Example VA

Figure 7A:
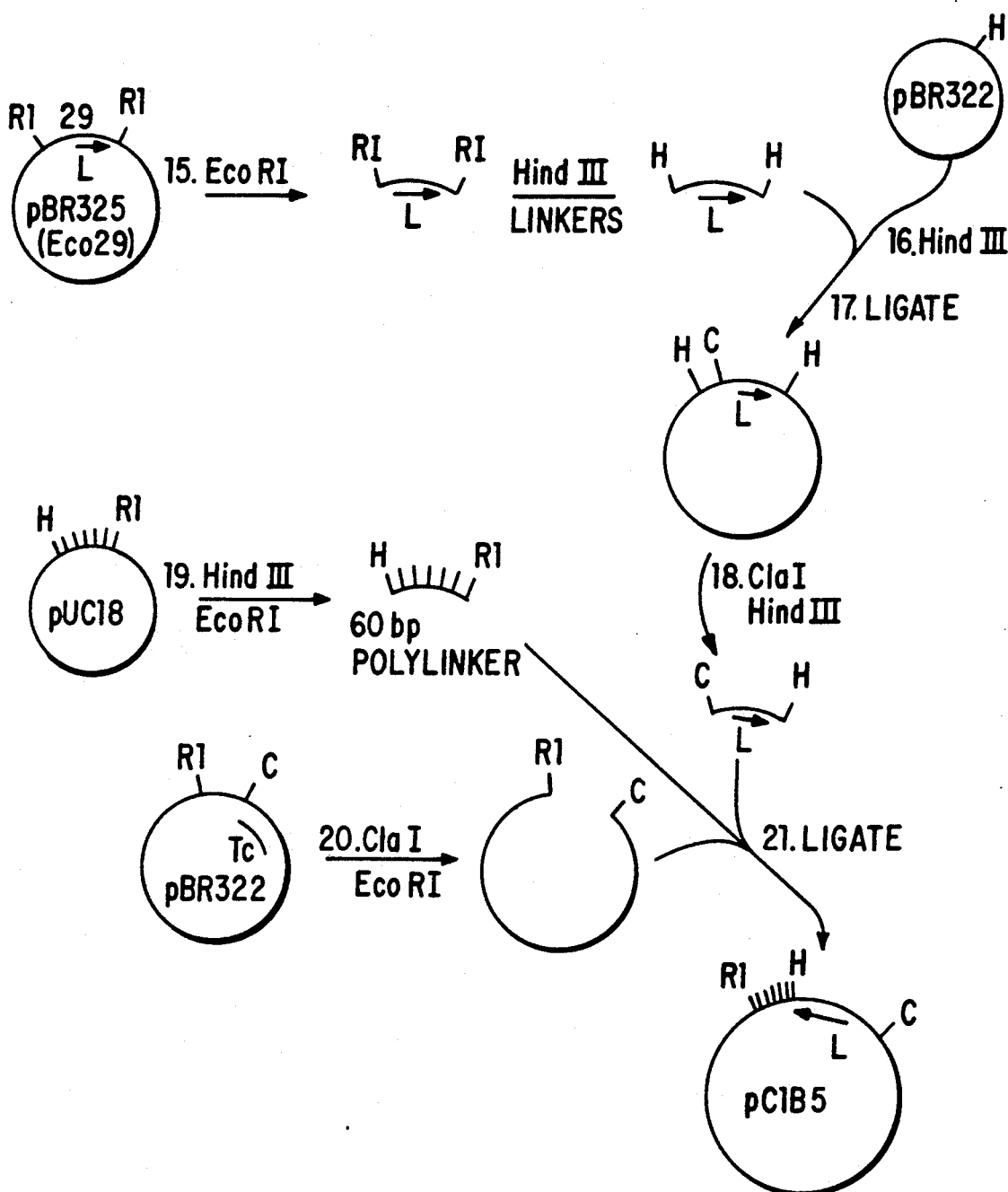
FIG. 7*a* describes the construction of pCIB5.
Figure 7B:
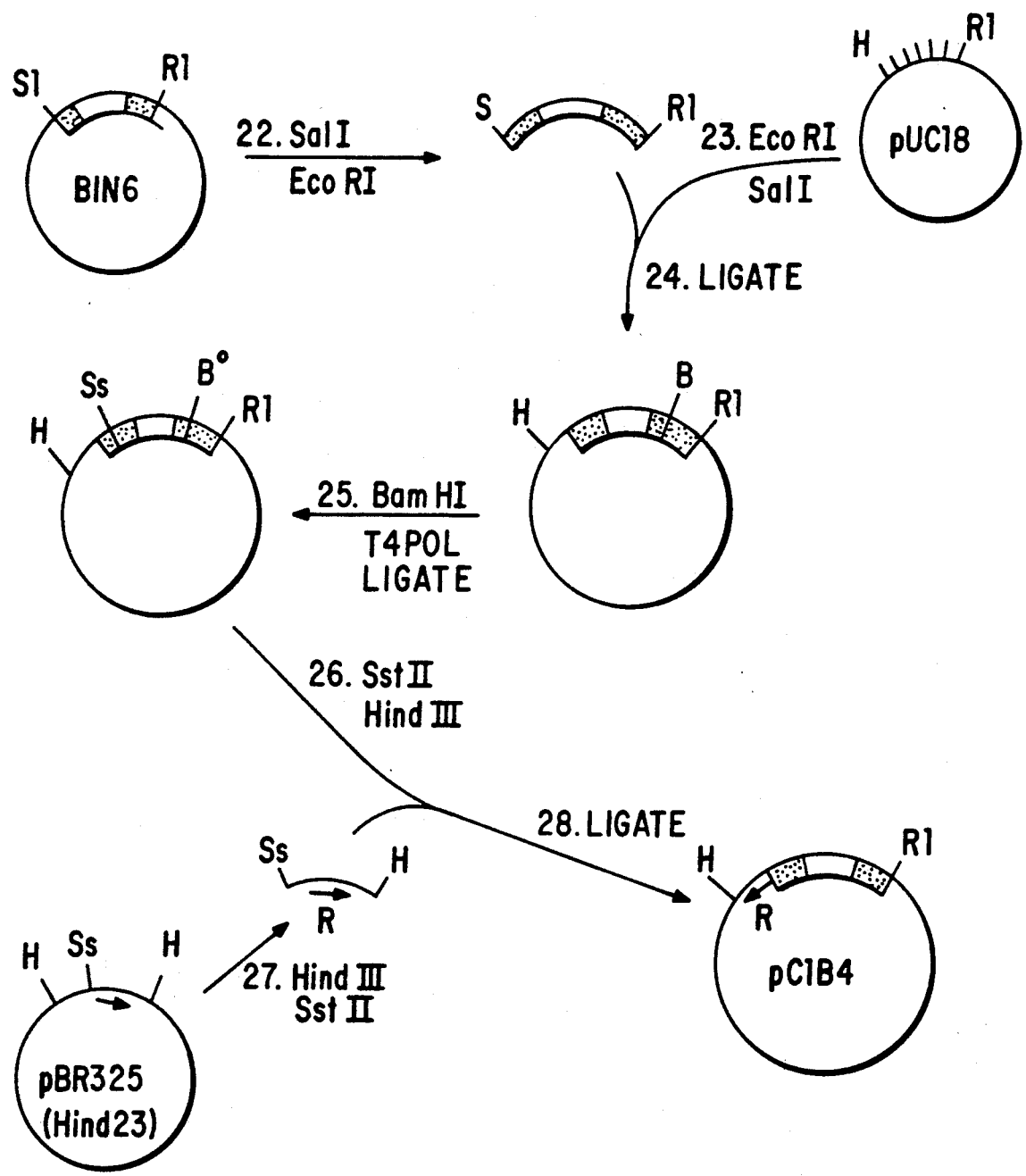
FIG. 7*b* describes the construction of pCIB4.
Figure 7C:
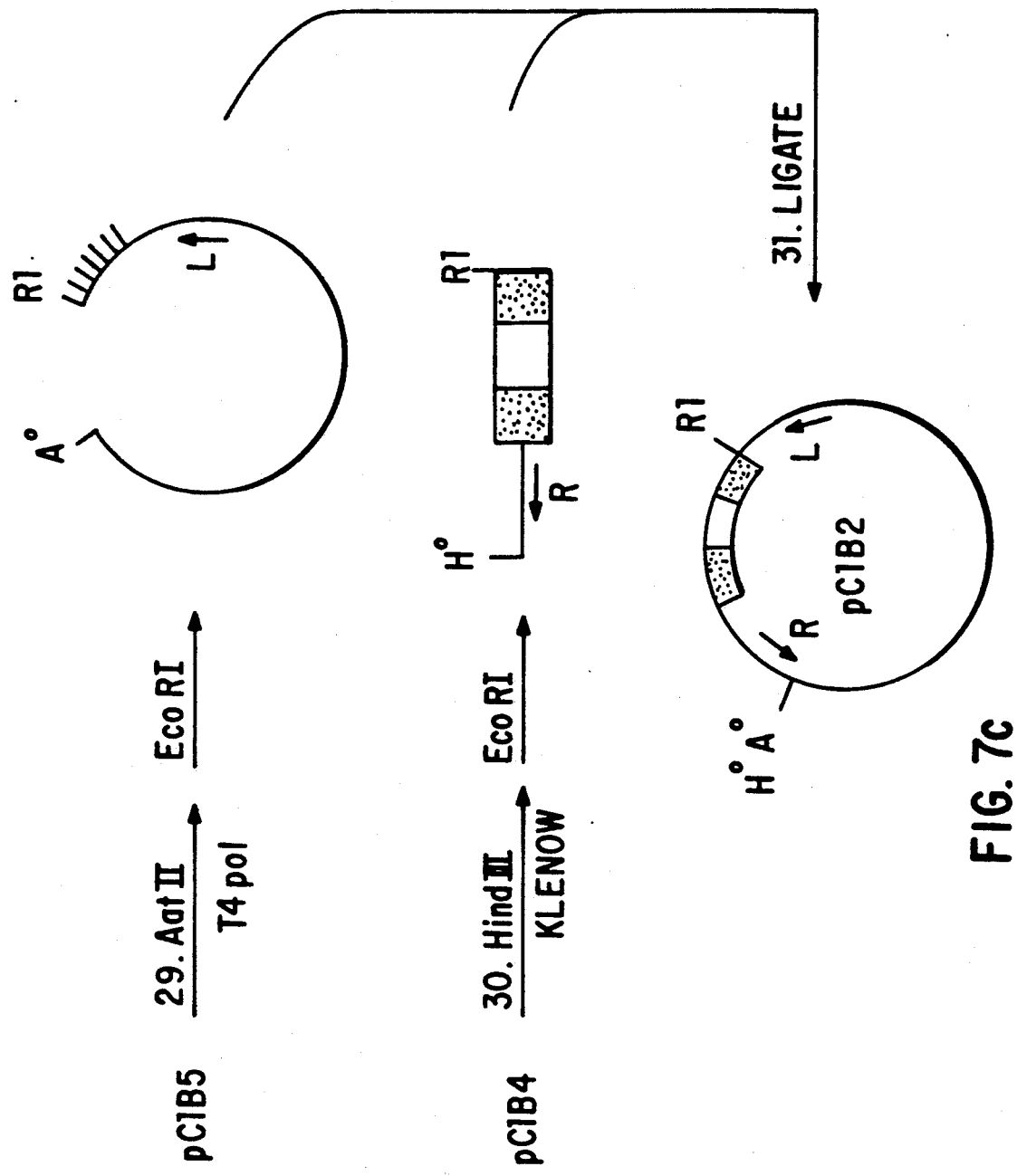
FIG. 7*c* describes the construction of pCIB2.
Figure 7D:
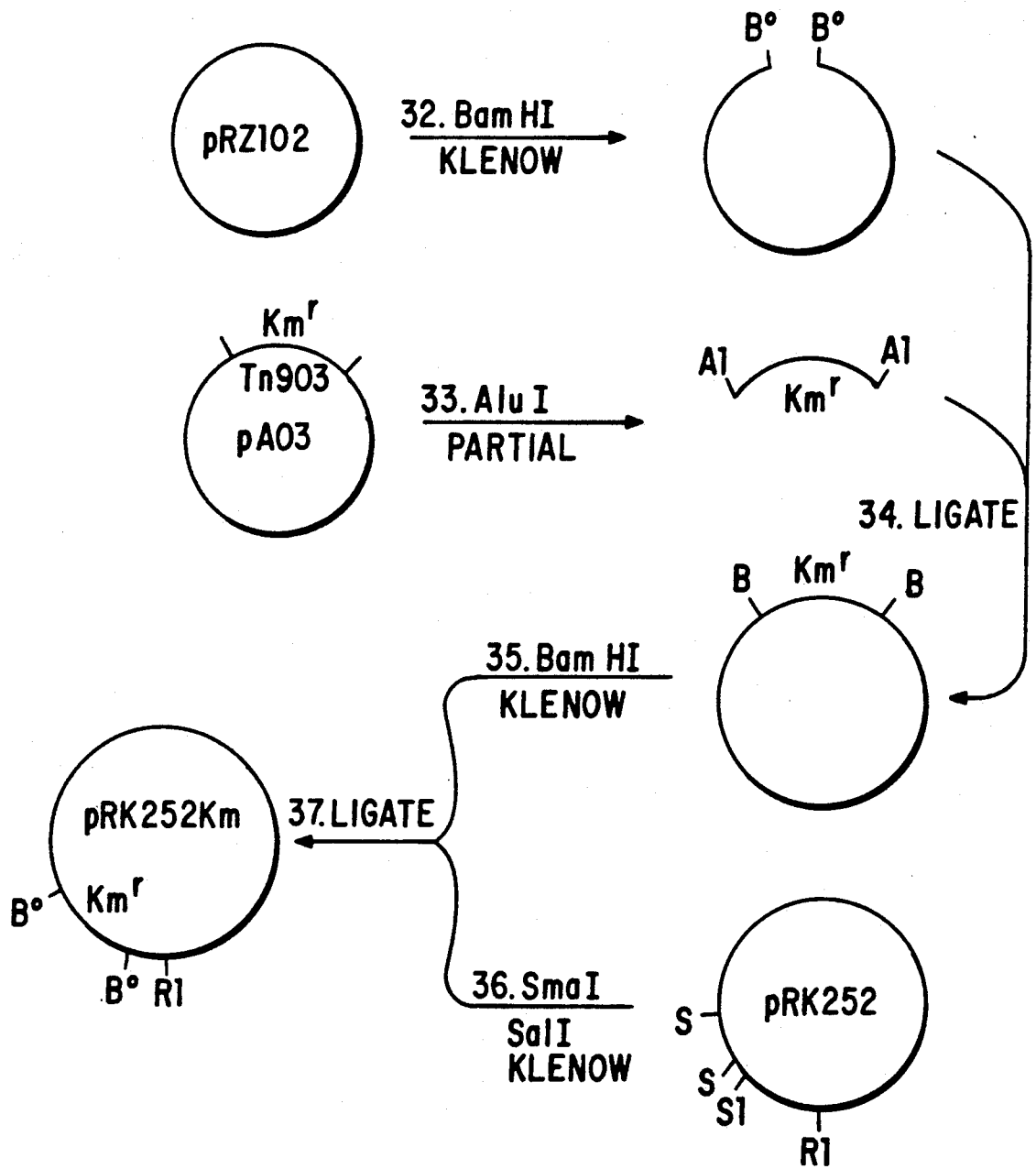
FIGS. 7*d* and *e* describe the construction of pCIB10.
Figure 7E:
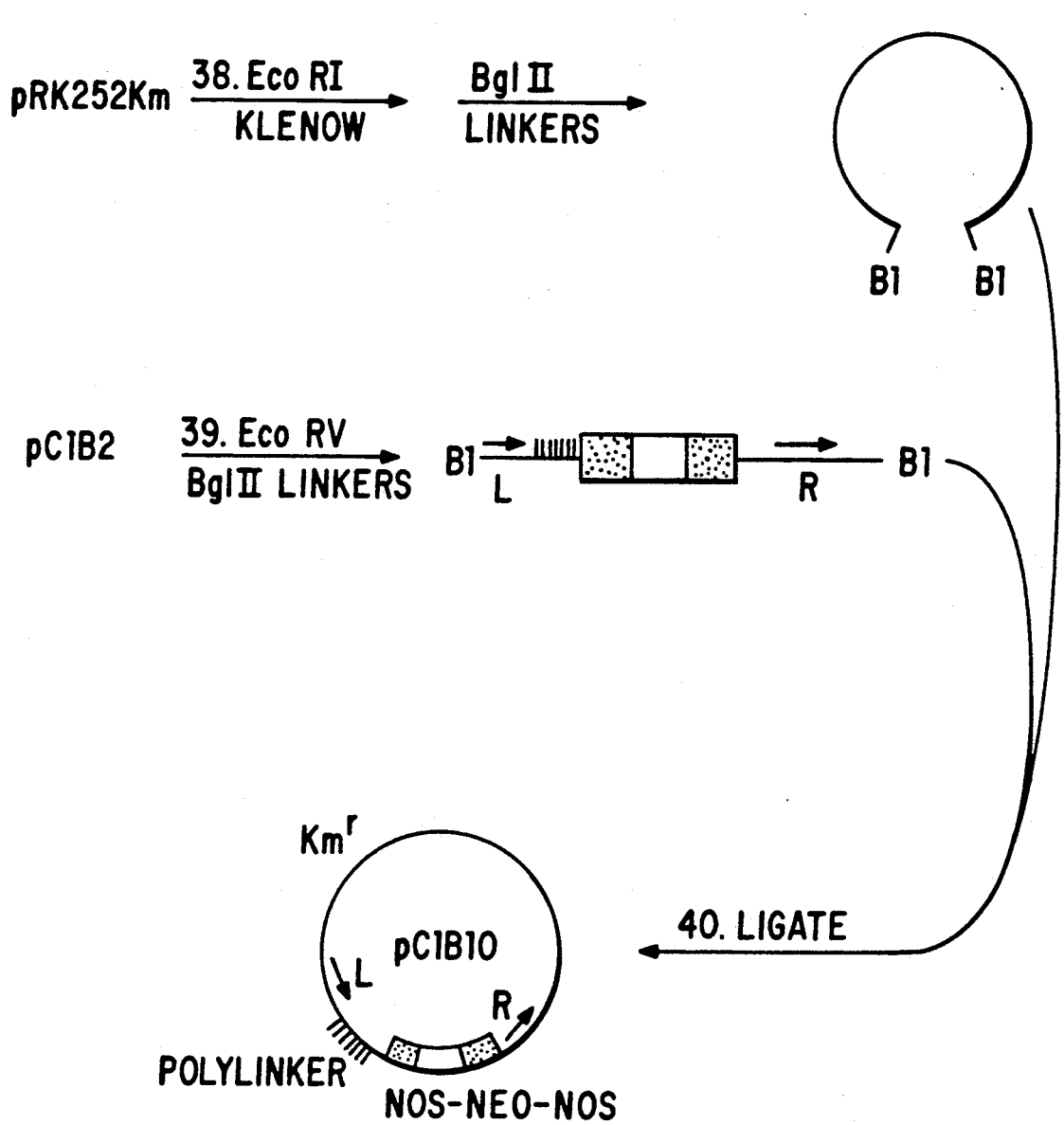
Figure 7G:
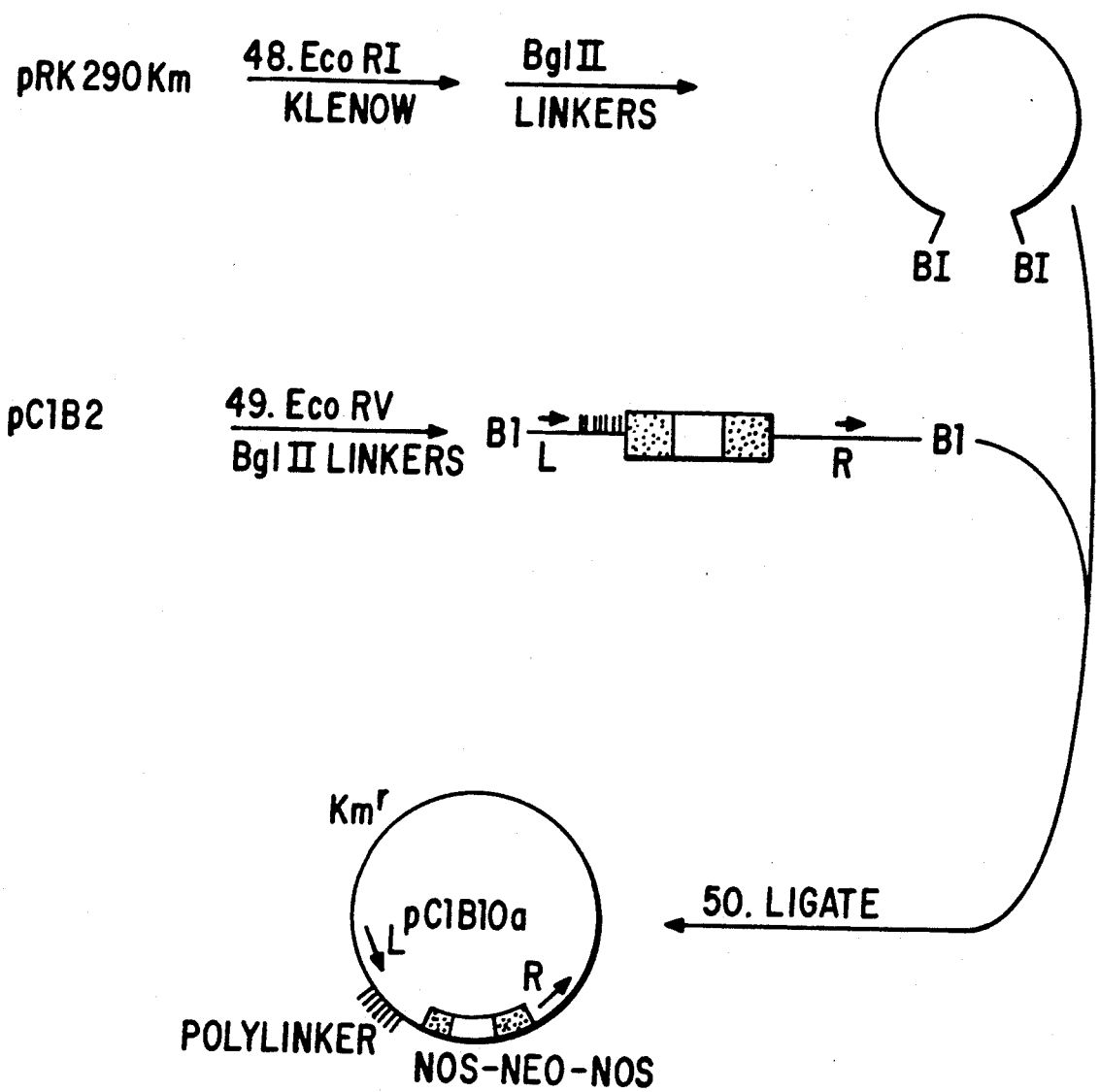
Figure 7F:
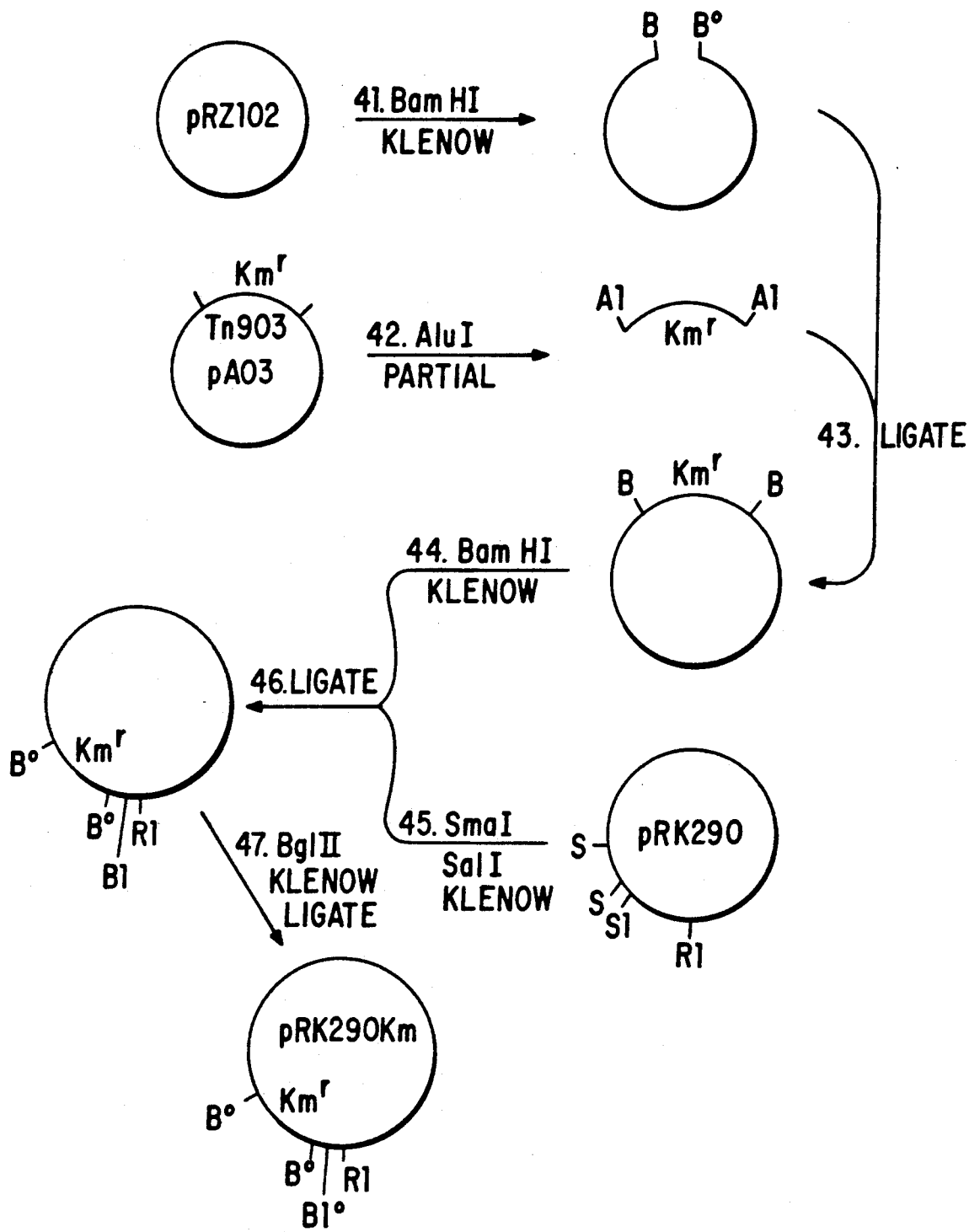

Construction of pCIBIOa (FIGS. 7*f* and *g*)

Example V can be repeated substituting the plasmid pRK290 (Ditta et al, Proc. Natl. Acad. Sci. USA, 77, 7347 (1980)) for pRK252.

41. The plasmid pRZ102 (Jorgensen, et al, Mol. Gen. Genet., 177, 65 (1979)) is digested with BamHI and filled in using Klenow.

42. An AluI partial digest of plasmid pA03 (Oka, et al, Nature, 276, 845 (1978)) is made.

43. The AluI digest is ligated into the restricted pRZ102, from step 32, selecting the desired transformants by resistance to kanamycin.

44. The resulting plasmid has the coding sequence of Tn903 present on a 1.05 kb BamHI fragment; this fragment is isolated after BamHI digestion and filling-in with Klenow.

45. The plasmid pRK290, a derivative of the broad host range plasmid RK2, is available from Dr. Don Helinski of the University of California, San Diego. pRK290 is digested with SmaI and SalI, filled in using Klenow, and the large fragment resulting from this digest isolated 46. The Tn903 containing fragment, isolated in step 35, is ligated into the large fragment from pRK290, constructing pRK290 Km.

47. The plasmid of step 46 is digested with BglII, filled in using Klenow and ligated, destroying its BglII site, to construct pRK290 Km.

48. The plasmid pRK290 Km is cut with EcoRI, blunt-ended using Klenow, and linkered with BglII linkered (New England Biolabs).

49. The plasmid pC182 is cut with EcoRV and is linkered with gIII linkers (New England Biolabs).

50. The BglII-linkered pCIB2 of step 39 is ligated into vector of step 47 constructing pCIB10a.

Example VI

Construction of pCIB23 and pCIB24, Vectors Targeting the GST Enzyme for the Chloroplast of Transformed Plants

Plasmid pSRS2.1, which contains the 5' sequence of the soybean small subunit (SSU) of ribulose bis-phosphate carboxylase (RuBPC) (Berry-Lowe et al., J. Mol. Appl. Genet., 1:483-498 (1982)) is obtained from Dr. Richard Meagher of the Department of Genetics, The University of Georgia, Athens, Georgia 30602. This plasmid is digested with EcoRI. The 2.1 kb fragment containing the soybean SSU 5' region is isolated from an agarose gel. The 2.1 kb EcoRI fragment is digested with DdeI. A 471 bp DdeI fragment is isolated. This fragment contains the transit peptide and a portion of the second exon.

The 471 bp DdeI fragment is treated with Klenow (New England Biolabs DNA polymerase). A kinased BglII linker (d(CAGATCTG) New England Biolabs) is ligated onto this fragment. This BglII fragment is digested with TaqI. The resulting TaqI fragments are treated with Klenow (Bethesda Research Labs DNA polymerase). The resulting blunt fragments are ligated onto kinased BamHI linkers (d(CGCGGATCCGCG) New England Biolabs) and purified. These BamHI fragments are digested with BglII and BamHI. A BamHI/BglII fragment of approximately 400 bp is purified; this fragment contains the SSU 5' region.

pCIB710 is cut with BamHI and treated with calf intestinal alkaline phosphatase. The 400 bp BamHI/BglII fragment is ligated into this pCIB710. This ligation is transformed into E. coli HB101 and transformants selected on ampicillin.

Transformants bearing the BamHI/BglII fragment in both orientations are found. pSCR2 has the 5' region of the transit peptide adjacent to the 35S promoter pSCR1 has the BamHI/BglII fragment in the opposite orientation.

pCIB12 is digested with BamHI and the 708 bp BamHI fragment bearing the GST gene is isolated. The plasmid pSCR2 is cut with bamHI and treated with calf intestinal alkaline phosphatase. The 708 bp BamHI fragment from pCIB12 is ligated into the BamHI treated pSCR2. The ligation is tranformed into HB101 and transformants are selected on ampicillin.

Transformants bearing the GST gene in both orientations to the 5' regulatory regions are found. The clone pCIB22 has the GST gene in appropriate orientation for transcription from the CaMV promoter. The clone pCIB21 has the GST gene in the opposite orientation. pCIB22 is digested with XbaI and EcoRI. The fragment carrying the chimeric gene is purified from a gel.

The plasmid pCIB10 is digested with XbaI and EcoRI. The XbaI/EcoRI fragment carrying the chimeric gene is ligated into the digested pCIB10 and transforants are selected by kanamycin resistance. The resulting plasmid, pCIB24, is a broad host range plasmid which bears the chimeric GST gene attached to a chloroplast transit peptide sequence.

Using similar manipulations and beginning with clone pCIB21 in place of pCIB22, a plasmid pCIB23 is constructed. This plasmid bears the GST gene in opposite orientation to the GST gene of pCIB24.

The plasmids are introduced into Agrobacterium strains in a manner similar to pCIB13 and pCIB14 above.

Example VII

Construction of pCIB542, An Agropine Vir Helper Plasmid Bearing a Spectinomycin Drug Resistance Gene in the Place of the T-DNA

The Ti plasmid, pTiBo542 (Sciaky, D., Montoya, A.L. & Chilton, M-D, Plasmid, 1:238-253 (1978)), is of interest because Agrobacteria bearing this Ti plasmid are able to infect the agronomically important legumes, alfalfa and bean (Hood , E.E., et al., Bio/Technology, 2:702-708 (1984)). The construction of a pTiBo542 derivative deleted on the T-DNA has been described (Hood, Elizabeth E., (1985) Ph.D. thesis; Washington University, St. Louis, Mo.). In this construction, named EHA101, the T-DNA was replaced by the kanamycin drug resistance gene. The parent of EHA101, A281, is on deposit at the ATCC, designated ATCC No. 53487.

A derivative of EHA101 having the kanamycin drug resistance gene replaced by a spectinomycin drug resistance gene was constructed. The plasmid p pi delta 307 (E. Hood, Washington University, thesis (1985)) has a 1.7 kb region of homology to the left side of Bam a of pTiBo542 (Hood, et al. (1984)) and an 8 kb region of homology to the right side of Bam2a of pTiBo542, separated by a unique gcoRI site. The plasmid pMON30, ATCC No. 67113, bears the spectinomycin/-streptomycin drug resistance gene from Tn7 (Hollingshead, S. and Vapnek, D., Plasmid, 13:17-30 (1985)). pMON30 was digested with EcoRI, the 5.5 kb fragment containing the spc/str gene isolated from an agarose gel, and ligated into EcoRI-restricted plasmid p pi delta 307. The desired recombinant is selected as a spectinomycin resistant (50 ug/ml) tetracycline resistant (10 ug/ml) transformant. This plasmid was transformed into Agrobacterium A136/EHA101 and selected by its streptomycinresistant, tetracycline-resistant, kanamycin-resistant phenotype. Homogenotes (Matzke, A.J.M. & Chilton, M-D, J. Mol. Appl. Genet., 1:39-49 (1981)) of EHA101 and the spectinomycin plasmid were selected after introduction of the eviction plasmid R751-pMG2 (Jacoby, G. et al., J. Bacteriol. , 127:1278-1285 (1976)) and selection on gentamycin (50 ug/ml) and spectinomycin. The desired homogenote had a gentamycin-resistant, spectinomycin-resistant, tetracycline-sensitive and kanamycin-sensitive phenotype. The structure of the resulting plasmid was confirmed by probing Southern blots.

Example VIII

Testing Plants for Atrazine Tolerance

Regenerated tobacco plants bearing the GST gene constructions pCIB14 are tolerant to atrazine as determined by several measures including:

(1) fluorescence induction; and
(2) ability of seedlings to grow on levels of atrazine toxic to control or wild-type plants.

Figure 5:
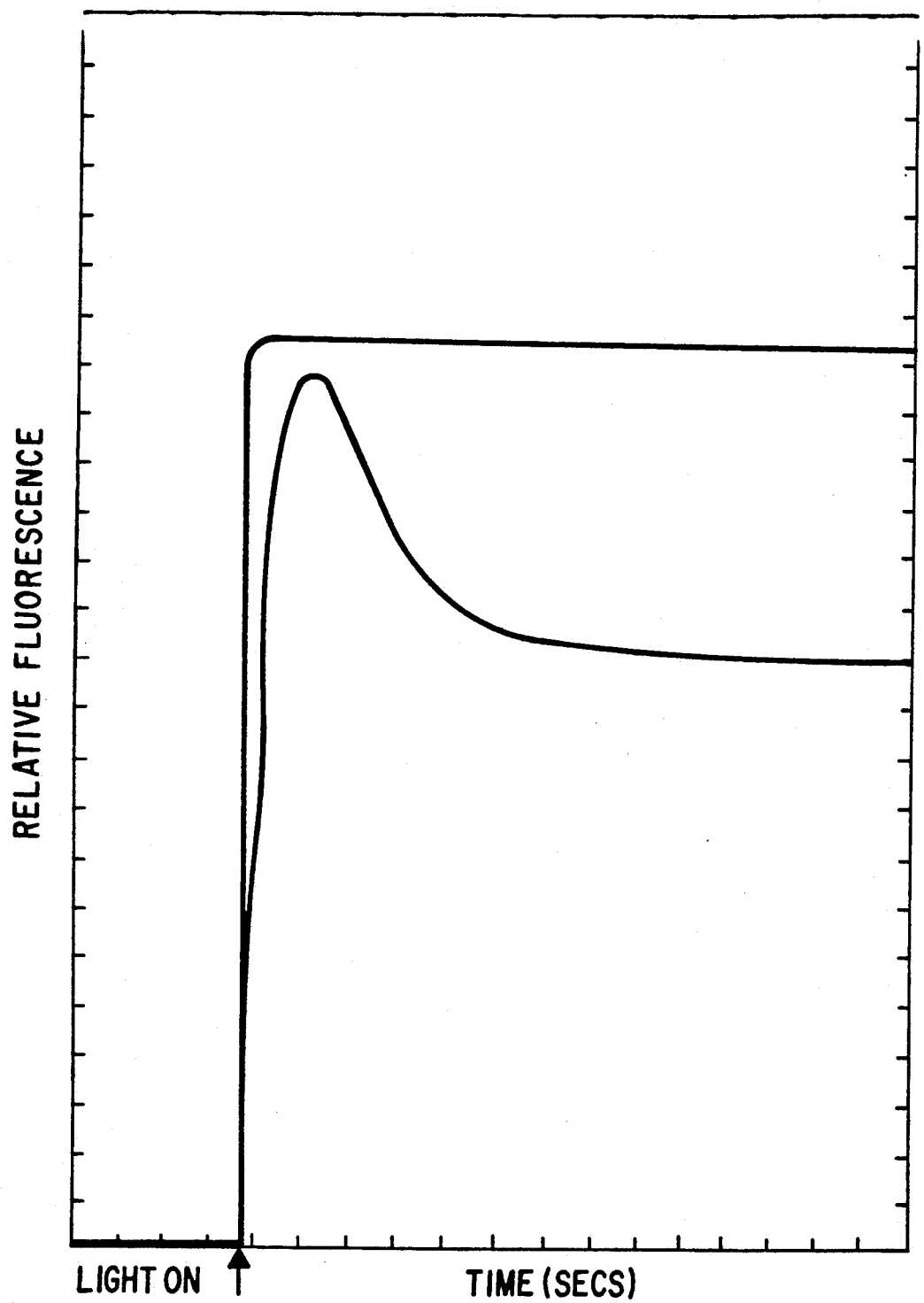
FIG. 5 shows fluorescence induction patterns typical of non-transgenic tobacco leaves. The upper curve is seen after the leaves have imbibed $10^{-5}$M atrazine for 48 hours. The lower curve is seen after inhibition with buffer solution alone.

Fluorescence induction assays are an indication of the status of the photochemical apparatus in the plant. (Voss et al., Weed Science, 32:675-680 (1984)). In such assays, leaf tissue is irradiated with light of characteristic wavelength and the resulting fluorescence at a second wavelength is recorded. FIG. 5 illustrates the fluorescence induction pattern typical of an excised tobacco (untransformed) leaf infiltrated with buffer solution by uptake through the cut petiole (leaf) (lower curve). One sees a sharp rise in fluorescence when the light is turned on, then a peak followed by a smooth decay of the signal over time. This pattern indicates that the chloroplasts are being excited by the incident light and fluoresce at a wave length characteristic of the system. At this point energy is channeled out of the photosystem as electrons flow through the electron transport pathway of photosystem II and I—this is indicated by the smooth decay curve of the fluorescence signal. If, however, the leaf is infiltrated with a solution of $10^{-5}$M atrazine, one sees a pattern such as the upper curve in FIG. 5. Here, the light energy is absorbed, the chloroplasts are exited and fluoresce, but no energy channeling occurs because electron flow is blocked at the quinone binding step of photosystem II. It is as if the photosystem were frozen in the excited state. Thus, one sees the sharp rise in fluorescence followed by no decay at all.

Figure 6:
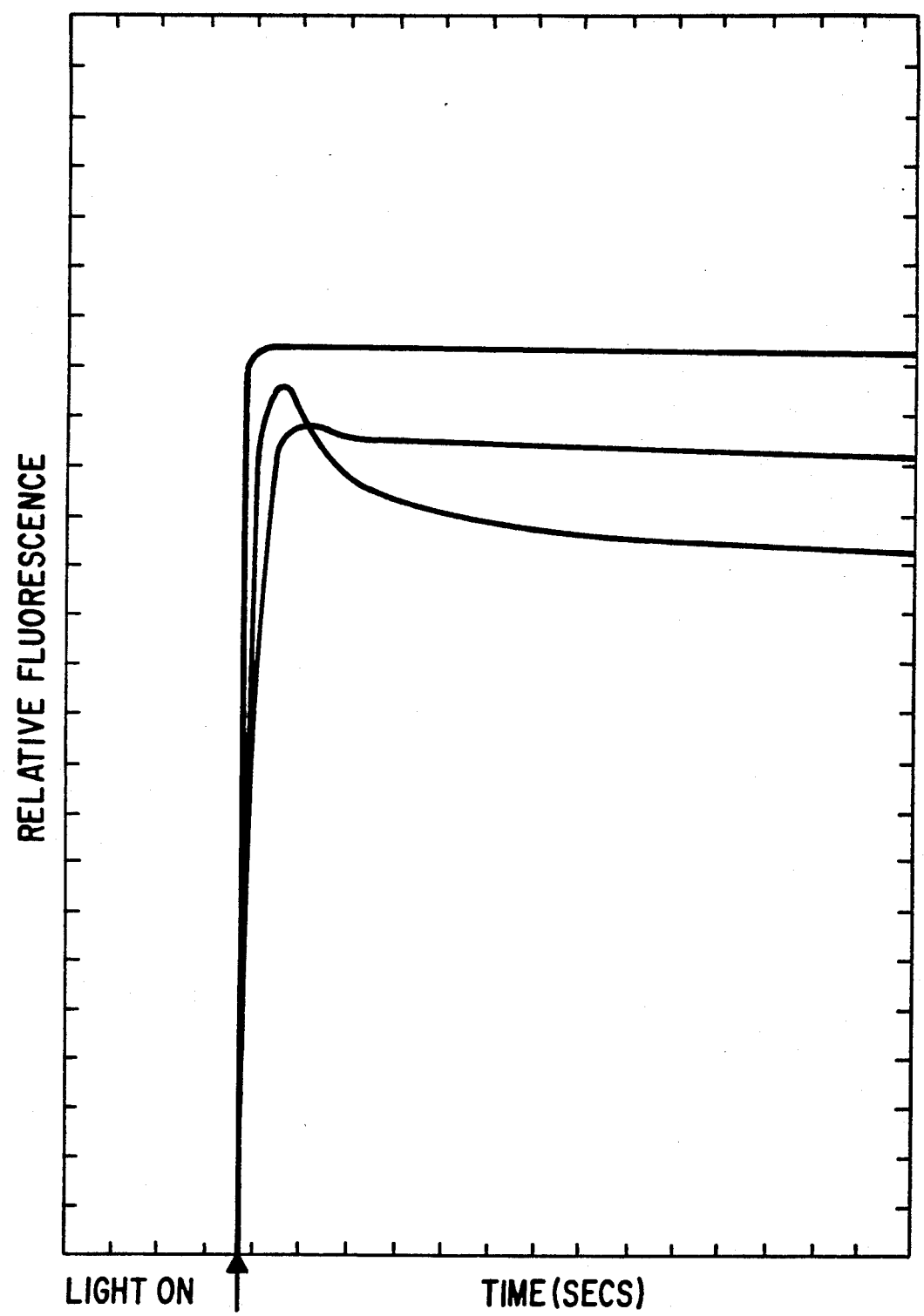
FIG. 6 shows fluorescence induction patterns seen in leaves of pCIB14 transgenic tobacco plants after imbibing $10^{-5}$M atrazine for 48 hours. Three classes of responses are seen: (i) no detoxification of atrazine, top curve; (ii) significant detoxification of atrazine, bottom curve; and (iii) some intermediate detoxification, middle curve.

When such measurements were carried out on genetically engineered tobacco plants according to this invention in the presence of $10^{-5}$M atrazine, all control plants show fluorescence induction patterns identical to the non-transgenic tobacco. When measurements were done on the experimental plants, they fell into three classes according to their fluorescence induction patterns (FIG. 6).

Some of the transgenic plants showed no evidence of atrazine detoxification (the top curve), some showed modest (middle curve) detoxification, and some showed significant (bottom curve) atrazine detoxification as evidenced by normal electron channeling through the photosystem. Of 27 plants characterized in this manner, 5 showed significant evidence of ability to detoxify atrazine.

Example IX

Agrobacterium Infection of Plant Material

The different genotypes of *Agrobacterium tumefaciens* were grown on AB minimal medium (Watson, B. et al., *J. Bacteriol.*, 123:255-264 (1975)) plus mannitol for 48 hours at 28° C. Bacteria were pelleted, resuspended in MSBN medium at a two-fold dilution, and held for three hours at 25° C. (MSBN medium comprised full strength major and minor salts of Murashsige and Skoog (KC Biologicals) with the following additions (in final concentrations): benzyladenine (1 mg/l); naphthylacetic acid (0.1 mg/l); myo-inositol (1 mg/l); nicotinni acid (1 mg/l); pyridoxine (1 mg/l); thiamine HCl (10 mg); and sucrose (30 gm/l). The pH was adjusted to 5.7 to 5.8. Leaf discs from in vitro cultured *Nicotiana tabacum cv. petite Havana SR*1 plants were floated on the bacterial suspension for 10 minutes in a modification of the method of Horsch, R. et al., *Science*, 227:1229-1231 (1985). They were then transferred to filter paper on MSBN without antibiotics. At 48 hours the leaf discs were dipped in liquid MSBN containing 500 mg/l of carbenicillin and transferred to solid selection medium containing 100 mg/l kanamycin and 500 mg/l carbenicillin.

Plant Maturation and Self Pollination

Shoots that arose from calli on selection medium were removed, transferred to OMS with 100 mg/l kanamycin and 250 mg/l carbenicillin, and development allowed to continue for three weeks. They were then planted in soil and moved to the greenhouse. Flowers formed four to eight weeks after transfer to the green house. As a flower opened and its anthers dihisced, forceps were used to remove the anthers and to self-pollinate each flower by rubbing the anthers on the stigma. Seed capsules matured in 40 days.

Testing Seed Progreny From Control, Control Transgenic and Experimental Transformed Plants Seeds were first removed axenically from mature capsules and stored in sterile petri dishes. Seeds were then placed on semi-soft seed germination medium (SGM) comprising the major and minor salts of Murashige & Skoog (KC Biologicals) at full strength, 1 mg/l of thiamine hydrochloride and 0.6% purified agar (Difco). Analytical grade atrazine was added to the medium at concentrations of $10^{-7}$M, $3 \times 10^{-7}$M, $5 \times ^{-7}$M, $8 \times 10^{-7}$M and $10^{-6}$M. The growth and survival of the seedlings were assessed on these concentrations and on zero level atrazine at 14 days; the results are given in Table 1 below. All control plants and control transgenic plants germinated but failed to grow past the cotyledon stage of growth at atrazine concentrations of $5 \times 10^{-7}$M or higher. Among the seedlings that grew from seeds of every selfed pCIB14 plant, approximately 75% remained green and produced primary leaves at $5 \times 10^{-7}$M, while seedlings on concentrations of atrazine of $8 \times 10^{-7}$M or higher formed only cotyledons before bleaching and dying. Although tolerant seedlings did not grow as well on the atrazine medium as on atrazine-free medium, they could easily be distinguished from the sensitive seedlings on the same medium.

| Seedling Genotype | Atrazine Concentration | | | | |
|---|---|---|---|---|---|
| | $10^{-7}$M | $3 \times 10^{-7}$M | $5 \times 10^{-7}$ | $8 \times 10^{-7}$M | $10^{-6}$M |
| Control | + | + | o | o | o |
| LBA 4404 | + | + | o | o | o |
| Bin 6 | + | + | o | o | o |
| pCIB 13 | + | + | o | o | o |
| pCIB 14 | + | + | + | o | o |

Table Legend. The difference in growth and survival between the progeny from pCIB14 transgenic plants and from all controls is shown. A positive growth response is indicated by + while o indicates no growth.

Table Legend: The difference in growth and survival between the progeny from pCIB14 transgenic plants and from all controls is shown. A positive growth response is indicated by + while o indicates no growth.

Although the foregoing invention has been described in some detail by way of illustration and example for purposes of clarity and understanding, it will be obvious that certain changes and modifications may be practiced within the scope of the invention, as limited only by the scope of the appended claims.

In the claims:

1. A transformed plant cell comprising a chimeric genetic sequence, said chimeric genetic sequence comprising a first genetic sequence coding for rat glutathione S-transferase, and one or more additional genetic sequences operably linked on either side of the first genetic sequence, wherein said first genetic sequence is capable of being expressed in a plant cell.

2. A transformed plant cell according to claim 1, wherein the first genetic sequences comprises the following nucleotide sequence:

```
    1 10                    13 0
tac agc atg ggg gat gct ccc gac tat gac aga agc cag
Tyr Ser Met Gly Asp Ala Pro Asp Tyr Asp Arg Ser Gln
```

-continued

```
               150                    1 70
tgg ctg agt gag aag ttc aaa ctg ggc ctg gac ttc ccc aat
Trp Leu Ser Glu Lys Phe Lys Leu Gly Leu Asp Phe Pro Asn 19 0                   210
ctg ccc tac tta att gat ggg tca cac aag atc acc cag agc aat
Leu Pro Tyr Leu Ile Asp Gly Ser His Lys Ile Thr Gln Ser Asn 2 30                  25 0
gcc atc ctg cgc tac ctt ggc cgg aag cac aac ctt tgt ggg gag
Ala Ile Leu Arg Tyr Leu Gly Arg Lys His Asn Leu Cys Gly Glu 270                    2 90                      31 0
aca gag gag gag agg att cgt gtg gac gtt ttg gag aac cag gct
Thr Glu Glu Glu Arg Ile Arg Val Asp Val Leu Glu Asn Gln Ala 330                       3 50
atg gac acc cgc cta cag ttg gcc atg gtc tgc tac agc cct
Met Asp Thr Arg Leu Gln Leu Ala Met Val Cys Tyr Ser Pro 37 0                     390
gac ttt gag aga aag aag cca gag tac tta gag ggt ctc cct
Asp Phe Glu Arg Lys Lys Pro Glu Tyr Leu Glu Gly Leu Pro 4 10                     43 0
gag aag atg aag ctt tac tcc gaa ttc ctg ggc aag cag cca tgg
Glu Lys Met Lys Leu Tyr Ser Glu Phe Leu Gly Lys Gln Pro Trp 450                      4 70
ttt gca ggg aac aag att acg tat gtg gat ttt ctt gtt tac gat
Phe Ala Gly Asn Lys Ile Thr Tyr Val Asp Phe Leu Val Tyr Asp 49 0                    510                         5 30
gtc ctt gat caa cac cgt ata ttt gaa ccc aag tgc ctg gac gcc
Val Leu Asp Gln His Arg Ile Phe Glu Pro Lys Cys Leu Asp Ala 55 0                       570
ttc cca aac ctg aag gac ttc gtg gct cgg ttt gag ggc ctg aag
Phe Pro Asn Leu Lys Asp Phe Val Ala Arg Phe Glu Gly Leu Lys 5 90                    61 0
aag ata tct gac tac atg aag agc ggc cgc ttc ctc tcc aag cca
Lys Ile Ser Asp Tyr Met Lys Ser Gly Arg Phe Leu Ser Lys Pro 630                   6 50
atc ttt gca aag atg gcc ttt tgg aac cca aag tag
Ile Phe Ala Lys Met Ala Phe Trp Asn Pro Lys End.
```

3. A transformed plant cell according to claim 1, wherein the first genetic sequences comprises the following nucleotide sequence:

```
       1 0                      30
atg cct atg aca ctg ggt tac tgg gac atc cgt ggg ctg gct cac
Met Pro Met Thr Leu Gly Tyr Trp Asp Ile Arg Gly Leu Ala His 50                    7 0                       90
gcc att cgc ctg ttc ctg gag tat aca gac aca agc tat gag gac
Ala Ile Arg Leu Phe Leu Glu Tyr Thr Asp Thr Ser Tyr Glu Asp 1 10                      13 0
aag aag tac agc atg ggg gat gct ccc gac tat gac aga agc cag
Lys Lys Tyr Ser Met Gly Asp Ala Pro Asp Tyr Asp Arg Ser Gln 150                      1 70
tgg ctg agt gag aag ttc aaa ctg ggc ctg gac ttc ccc aat ctg
Trp Leu Ser Glu Lys Phe Lys Leu Gly Leu Asp Phe Pro Asn Leu 19 0                     210
ccc tac tta att gat ggg tca cac aag atc acc cag agc aat gcc
Pro Tyr Leu Ile Asp Gly Ser His Lys Ile Thr Gln Ser Asn Ala 2 30                 25 0                   270
atc ctg cgc tac ctt ggc cgg aag cac aac ctt tgt ggg gag aca
Ile Leu Arg Tyr Leu Gly Arg Lys His Asn Leu Cys Gly Glu Thr 2 90                       31 0
gag gag gag agg att cgt gtg gac gtt ttg gag aac cag gct atg
Glu Glu Glu Arg Ile Arg Val Asp Val Leu Glu Asn Gln Ala Met
```

```
                 330                    3 50
gac acc cgc cta cag ttg gcc atg gtc tgc tac agc cct gac ttt
Asp Thr Arg Leu Gln Leu Ala Met Val Cys Tyr Ser Pro Asp Phe 37 0                     390
gag aga aag aag cca gag tac tta gag ggt ctc cct gag aag atg
Glu Arg Lys Lys Pro Glu Tyr Leu Glu Gly Leu Pro Glu Lys Met 4 10                     43 0                   450
aag ctt tac tcc gaa ttc ctg ggc aag cag cca tgg ttt gca ggg
Lys Leu Tyr Ser Glu Phe Leu Gly Lys Gln Pro Trp Phe Ala Gly 4 70                       49 0
aac aag att acg tat gtg gat ttt ctt gtt tac gat gtc ctt gat
Asn Lys Ile Thr Tyr Val Asp Phe Leu Val Tyr Asp Val Leu Asp 510                      5 30
caa cac cgt ata ttt gaa ccc aag tgc ctg gac gcc ttc cca aac
Gln His Arg Ile Phe Glu Pro Lys Cys Leu Asp Ala Phe Pro Asn 55 0                       570
ctg aag gac ttc gtg gct cgg ttt gag ggc ctg aag aag ata tct
Leu Lys Asp Phe Val Ala Arg Phe Glu Gly Leu Lys Lys Ile Ser 5 90                   61 0                   630
gac tac atg aag agc ggc cgc ttc ctc tcc aag cca atc ttt gca
Asp Tyr Met Lys Ser Gly Arg Phe Leu Ser Lys Pro Ile Phe Ala 6 50
aag atg gcc ttt tgg aac cca aag tag
Lys Met Ala Phe Trp Asn Pro Lys End.
```

4. A transformed plant cell according to claim 1, wherein the first genetic sequences comprises the following nucleotide sequence:

```
                   30                     50
atg ccc atg aca ctg ggt tac tgg gac atc cgt ggg cta gcg cat
Met Pro Met Thr Leu Gly Tyr Trp Asp Ile Arg Gly Leu Ala His 70                       90
gcc atc cgc ctg ctc ctg gaa tac aca gac tcg agc tat gag gag
Ala Ile Arg Leu Leu Leu Glu Tyr Thr Asp Ser Ser Tyr Glu Glu 110                      130
aag aga tac acc atg gga gac gct ccc gac ttt gac aga agc
Lys Arg Tyr Thr Met Gly Asp Ala Pro Asp Phe Asp Arg Ser 150                    170                      190
cag tgg ctg aat gag aag ttc aaa ctg ggc ctg gac ttc ccc aat
Gln Trp Leu Asn Glu Lys Phe Lys Leu Gly Leu Asp Phe Pro Asn 210                     230
ctg ccc tac tta att gat gga tca cac aag atc acc cag agc aat
Leu Pro Tyr Leu Ile Asp Gly Ser His Lys Ile Thr Gln Ser Asn 250                      270
gcc atc ctg cgc tat ctt ggc cgc aag cac aac ctg tgt ggg gag
Ala Ile Leu Arg Tyr Leu Gly Arg Lys His Asn Leu Cys Gly Glu 290                       310
aca gaa gag gag agg att cgt gtg gac att ctg gag aat cag ctc
Thr Glu Glu Glu Arg Ile Arg Val Asp Ile Leu Glu Asn Gln Leu 330                      350
atg gac aac cgc atg gtg ctg gcg aga ctt tgc tat aac cct
Met Asp Asn Arg Met Val Leu Ala Arg Leu Cys Tyr Asn Pro 370                    390                    410
gac ttt gag aag ctg aag cca ggg tac atg gag caa atg cct gga
Asp Phe Glu Lys Leu Lys Pro Gly Tyr Met Glu Gln Met Pro Gly 430                      450
atg atg cgg ctt tac tcc gag ttc ctg ggc aag cgg cca tgg ttt
Met Met Arg Leu Tyr Ser Glu Phe Leu Gly Lys Arg Pro Trp Phe 470                      490
gca ggg gac aag atc acc ttt gtg gat ttc att gct tac gat gtt
Ala Gly Asp Lys Ile Thr Phe Val Asp Phe Ile Ala Tyr Asp Val
```

-continued
```
       510                           530
ctt gag agg aac caa gtg ttt gag gcc acg tgc ctg gac gcg ttc
Leu Glu Arg Asn Gln Val Phe Glu Ala Thr Cys Leu Asp Ala Phe 550                  570                   590
cca aac ctg aag gat ttc ata gcg cgc ttt gag ggc ctg aag aag
Pro Asn Leu Lys Asp Phe Ile Ala Arg Phe Glu Gly Leu Lys Lys 610                           630
atc tcc gac tac atg aag tcc agc cgc ttc ctc cca aga cct ctg
Ile Ser Asp Tyr Met Lys Ser Ser Arg Phe Leu Pro Arg Pro Leu 650                    670
ttc aca aag atg gct att tgg ggc agc aag tag
Phe Thr Lys Met Ala Ile Trp Gly Ser Lys End.
```

5. A transformed plant cell according to claim 1, wherein the additional genetic sequences contains a plant promoter selected from the group consisting of nos, ocs and CaMV promoters, the promoter of a soybean small subunit of ribulose bis-phosphate carboxylase, and the promoter of a chlorophyll a/b binding protein.

6. A recombinant DNA molecule comprising a plant promoter operably linked with a chimeric non-native genetic sequence coding for rat glutathione S-transferase, wherein said recombinant genetic sequence is capable of being expressed in a plant cell.

7. A recombinant DNA molecule according to claim 6, wherein the genetic sequences comprises the following nucleotide sequence:

```
         1 10                           1 30
tac agc atg ggg gat gct ccc gac tat gac aga agc cag
Tyr Ser Met Gly Asp Ala Pro Asp Tyr Asp Arg Ser Gln 150                      1 70
tgg ctg agt gag aag ttc aaa ctg ggc ctg gac ttc ccc aat ctg
Trp Leu Ser Glu Lys Phe Lys Leu Gly Leu Asp Phe Pro Asn Leu 19 0                    210
ccc tac tta att gat ggg tca cac aag atc acc cag agc aat gcc
Pro Tyr Leu Ile Asp Gly Ser His Lys Ile Thr Gln Ser Asn Ala 2 30              25 0                     270
atc ctg cgc tac ctt ggc cgg aag cac aac ctt tgt ggg gag aca
Ile Leu Arg Tyr Leu Gly Arg Lys His Asn Leu Cys Gly Glu Thr 2 90                         31 0
gag gag gag agg att cgt gtg gac gtt ttg gag aac cag gct atg
Glu Glu Glu Arg Ile Arg Val Asp Val Leu Glu Asn Gln Ala Met 330                      3 50
gac acc cgc cta cag ttg gcc atg gtc tgc tac agc cct gac ttt
Asp Thr Arg Leu Gln Leu Ala Met Val Cys Tyr Ser Pro Asp Phe 37 0                           390
gag aga aag aag cca gag tac tta gag ggt ctc cct gag aag atg
Glu Arg Lys Lys Pro Glu Tyr Leu Glu Gly Leu Pro Glu Lys Met 4 10                   43 0                   450
aag ctt tac tcc gaa ttc ctg ggc aag cag cca tgg ttt gca ggg
Lys Leu Tyr Ser Glu Phe Leu Gly Lys Gln Pro Trp Phe Ala Gly 4 70                           49 0
aac aag att acg tat gtg gat ttt ctt gtt tac gat gtc ctt gat
Asn Lys Ile Thr Tyr Val Asp Phe Leu Val Tyr Asp Val Leu Asp 510                     5 30
caa cac cgt ata ttt gaa ccc aag tgc ctg gac gcc ttc cca aac
Gln His Arg Ile Phe Glu Pro Lys Cys Leu Asp Ala Phe Pro Asn 55 0                       570
ctg aag gac ttc gtg gct cgg ttt gag ggc ctg aag aag ata tct
Leu Lys Asp Phe Val Ala Arg Phe Glu Gly Leu Lys Lys Ile Ser
```

```
  5 90                    61 0                     630
gac tac atg aag agc ggc cgc ttc ctc tcc aag cca atc ttt gca
Asp Tyr Met Lys Ser Gly Arg Phe Leu Ser Lys Pro Ile Phe Ala 6 50
aag atg gcc ttt tgg aac cca aag tag
Lys Met Ala Phe Trp Asn Pro Lys End.
```

8. A recombinant DNA molecule according to claim 6, wherein the genetic sequences comprises the following nucleotide sequence:

```
        1 0                         30
atg cct atg aca ctg ggt tac tgg gac atc cgt ggg ctg gct cac
Met Pro Met Thr Leu Gly Tyr Trp Asp Ile Arg Gly Leu Ala His 50                 7 0                     90
gcc att cgc ctg ttc ctg gag tat aca gac aca agc tat gag gac
Ala Ile Arg Leu Phe Leu Glu Tyr Thr Asp Thr Ser Tyr Glu Asp 1 10                       13 0
aag aag tac agc atg ggg gat gct ccc gac tat gac aga agc cag
Lys Lys Tyr Ser Met Gly Asp Ala Pro Asp Tyr Asp Arg Ser Gln 150                       1 70
tgg ctg agt gag aag ttc aaa ctg ggc ctg gac ttc ccc aat ctg
Trp Leu Ser Glu Lys Phe Lys Leu Gly Leu Asp Phe Pro Asn Leu 19 0                     210
ccc tac tta att gat ggg tca cac aag atc acc cag agc aat gcc
Pro Tyr Leu Ile Asp Gly Ser His Lys Ile Thr Gln Ser Asn Ala 2 30                 25 0                     270
atc ctg cgc tac ctt ggc cgg aag cac aac ctt tgt ggg gag aca
Ile Leu Arg Tyr Leu Gly Arg Lys His Asn Leu Cys Gly Glu Thr 2 90                          31 0
gag gag gag agg att cgt gtg gac gtt ttg gag aac cag gct atg
Glu Glu Glu Arg Ile Arg Val Asp Val Leu Glu Asn Gln Ala Met 330                      3 50
gac acc cgc cta cag ttg gcc atg gtc tgc tac agc cct gac ttt
Asp Thr Arg Leu Gln Leu Ala Met Val Cys Tyr Ser Pro Asp Phe 37 0                       390
gag aga aag aag cca gag tac tta gag ggt ctc cct gag aag atg
Glu Arg Lys Lys Pro Glu Tyr Leu Glu Gly Leu Pro Glu Lys Met 4 10                    43 0                    450
aag ctt tac tcc gaa ttc ctg ggc aag cag cca tgg ttt gca ggg
Lys Leu Tyr Ser Glu Phe Leu Gly Lys Gln Pro Trp Phe Ala Gly 4 70                          49 0
aac aag att acg tat gtg gat ttt ctt gtt tac gat gtc ctt gat
Asn Lys Ile Thr Tyr Val Asp Phe Leu Val Tyr Asp Val Leu Asp 510                        5 30
caa cac cgt ata ttt gaa ccc aag tgc ctg gac gcc ttc cca aac
Gln His Arg Ile Phe Glu Pro Lys Cys Leu Asp Ala Phe Pro Asn 55 0                      570
ctg aag gac ttc gtg gct cgg ttt gag ggc ctg aag aag ata tct
Leu Lys Asp Phe Val Ala Arg Phe Glu Gly Leu Lys Lys Ile Ser 5 90                     61 0                    630
gac tac atg aag agc ggc cgc ttc ctc tcc aag cca atc ttt gca
Asp Tyr Met Lys Ser Gly Arg Phe Leu Ser Lys Pro Ile Phe Ala 6 50
aag atg gcc ttt tgg aac cca aag tag
Lys Met Ala Phe Trp Asn Pro Lys End.
```

9. A recombinant DNA molecule according to claim 6, wherein the genetic sequences comprises the following nucleotide sequence:

```
                    30                   50
atg ccc atg aca ctg ggt tac tgg gac atc cgt ggg cta gcg cat
Met Pro Met Thr Leu Gly Tyr Trp Asp Ile Arg Gly Leu Ala His 70                   90
gcc atc cgc ctg ctc ctg gaa tac aca gac tcg agc tat gag gag
Ala Ile Arg Leu Leu Leu Glu Tyr Thr Asp Ser Ser Tyr Glu Glu 110                  130
aag aga tac acc atg gga gac gct ccc gac ttt gac aga agc
Lys Arg Tyr Thr Met Gly Asp Ala Pro Asp Phe Asp Arg Ser 150              170             190
cag tgg ctg aat gag aag ttc aaa ctg ggc ctg gac ttc ccc aat
Gln Trp Leu Asn Glu Lys Phe Lys Leu Gly Leu Asp Phe Pro Asn 210                  230
ctg ccc tac tta att gat gga tca cac aag atc acc cag agc aat
Leu Pro Tyr Leu Ile Asp Gly Ser His Lys Ile Thr Gln Ser Asn 250                  270
gcc atc ctg cgc tat ctt ggc cgc aag cac aac ctg tgt ggg gag
Ala Ile Leu Arg Tyr Leu Gly Arg Lys His Asn Leu Cys Gly Glu 290                  310
aca gaa gag gag agg att cgt gtg gac att ctg gag aat cag ctc
Thr Glu Glu Glu Arg Ile Arg Val Asp Ile Leu Glu Asn Gln Leu 330                  350
atg gac aac cgc atg gtg ctg gcg aga ctt tgc tat aac cct
Met Asp Asn Arg Met Val Leu Ala Arg Leu Cys Tyr Asn Pro 370             390                 410
gac ttt gag aag ctg aag cca ggg tac atg gag caa atg cct gga
Asp Phe Glu Lys Leu Lys Pro Gly Tyr Met Glu Gln Met Pro Gly 430                 450
atg atg cgg ctt tac tcc gag ttc ctg ggc aag cgg cca tgg ttt
Met Met Arg Leu Tyr Ser Glu Phe Leu Gly Lys Arg Pro Trp Phe 470                 490
gca ggg gac aag atc acc ttt gtg gat ttc att gct tac gat gtt
Ala Gly Asp Lys Ile Thr Phe Val Asp Phe Ile Ala Tyr Asp Val 510                 530
ctt gag agg aac caa gtg ttt gag gcc acg tgc ctg gac gcg ttc
Leu Glu Arg Asn Gln Val Phe Glu Ala Thr Cys Leu Asp Ala Phe 550             570             590
cca aac ctg aag gat ttc ata gcg cgc ttt gag ggc ctg aag aag
Pro Asn Leu Lys Asp Phe Ile Ala Arg Phe Glu Gly Leu Lys Lys 610                 630
atc tcc gac tac atg aag tcc agc cgc ttc ctc cca aga cct ctg
Ile Ser Asp Tyr Met Lys Ser Ser Arg Phe Leu Pro Arg Pro Leu 650                 670
ttc aca aag atg gct att tgg ggc agc aag tag
Phe Thr Lys Met Ala Ile Trp Gly Ser Lys End.
```

10. A recombinant DNA molecule according to claim 6, wherein the plant promoter is selected from the group consisting of nos, ocs and CaMV promoters, the promoter of a soybean small subunit of ribulose bisphosphate carboxylase, and the promoter of a chlorophyll a/b binding protein.

11. A recombinant DNA vector comprising a plant promoter operably linked to a chimeric non-native genetic sequence coding for rat glutathione S-transferase, wherein said recombinant genetic sequence is capable of being expressed in the plant cell.

12. A recombinant DNA vector according to claim 11, wherein the genetic sequences comprises the following nucleotide sequence:

```
            1 10               13 0
tac agc atg ggg gat gct ccc gac tat gac aga agc cag
Tyr Ser Met Gly Asp Ala Pro Asp Tyr Asp Arg Ser Gln 150                1 70
tgg ctg agt gag aag ttc aaa ctg ggc ctg gac ttc ccc aat ctg
Trp Leu Ser Glu Lys Phe Lys Leu Gly Leu Asp Phe Pro Asn Leu 19 0                210
ccc tac tta att gat ggg tca cac aag atc acc cag agc aat gcc
Pro Tyr Leu Ile Asp Gly Ser His Lys Ile Thr Gln Ser Asn Ala 2 30             25 0              270
atc ctg cgc tac ctt ggc cgg aag cac aac ctt tgt ggg gag aca
Ile Leu Arg Tyr Leu Gly Arg Lys His Asn Leu Cys Gly Glu Thr 2 90               31 0
gag gag gag agg att cgt gtg gac gtt ttg gag aac cag gct atg
Glu Glu Glu Arg Ile Arg Val Asp Val Leu Glu Asn Gln Ala Met 330               3 50
gac acc cgc cta cag ttg gcc atc gtc tgc tac agc cct gac ttt
Asp Thr Arg Leu Gln Leu Ala Met Val Cys Tyr Ser Pro Asp Phe 37 0              390
gag aga aag aag cca gag tac tta gag ggt ctc cct gag aag atg
Glu Arg Lys Lys Pro Glu Tyr Leu Glu Gly Leu Pro Glu Lys Met 4 10             43 0              450
aag ctt tac tcc gaa ttc ctg ggc aag cag cca tgg ttt gca ggg
Lys Leu Tyr Ser Glu Phe Leu Gly Lys Gln Pro Trp Phe Ala Gly 4 70              49 0
aac aag att acg tat gtg gat ttt ctt gtt tac gat gtc ctt gat
Asn Lys Ile Thr Tyr Val Asp Phe Leu Val Tyr Asp Val Leu Asp 510              5 30
caa cac cgt ata ttt gaa ccc aag tgc ctg gac gcc ttc cca aac
Gln His Arg Ile Phe Glu Pro Lys Cys Leu Asp Ala Phe Pro Asn 55 0              570
ctg aag gac ttc gtg gct cgg ttt gag ggc ctg aag aag ata tct
Leu Lys Asp Phe Val Ala Arg Phe Glu Gly Leu Lys Lys Ile Ser 5 590            61 0             630
gac tac atg aag agc ggc cgc ttc ctc tcc aag cca atc ttt gca
Asp Tyr Met Lys Ser Gly Arg Phe Leu Ser Lys Pro Ile Phe Ala 6 50
aag atg gcc ttt tgg aac cca aag tag
Lys Met Ala Phe Trp Asn Pro Lys End.
```

13. A recombinant DNA vector according to claim 11, wherein the genetic sequences comprises the following nucleotide sequence:

```
            1 0                30
atg cct atg aca ctg ggt tac tgg gac atc cgt ggg ctg gct cac
Met Pro Met Thr Leu Gly Tyr Trp Asp Ile Arg Gly Leu Ala His 50                70             90
gcc att cgc ctg ttc ctg gag tat aca gac aca agc tat gag gac
Ala Ile Arg Leu Phe Leu Glu Tyr Thr Asp Thr Ser Tyr Glu Asp 1 10               13 0
aag aag tac agc atg ggg gat gct ccc gac tat gac aga agc cag
Lys Lys Tyr Ser Met Gly Asp Ala Pro Asp Tyr Asp Arg Ser Gln 150                1 70
tgg ctg agt gag aag ttc aaa ctg ggc ctg gac ttc ccc aat ctg
Trp Leu Ser Glu Lys Phe Lys Leu Gly Leu Asp Phe Pro Asn Leu 19 0                210
ccc tac tta att gat ggg tca cac aag atc acc cag agc aat gcc
Pro Tyr Leu Ile Asp Gly Ser His Lys Ile Thr Gln Ser Asn Ala 2 30             25 0              270
atc ctg cgc tac ctt ggc cgg aag cac aac ctt tgt ggg gag aca
Ile Leu Arg Tyr Leu Gly Arg Lys His Asn Leu Cys Gly Glu Thr
```

-continued

```
             290              310
gag gag gag agg att cgt gtg gac gtt ttg gag aac cag gct atg
Glu Glu Glu Arg Ile Arg Val Asp Val Leu Gly Asn Gln Ala Met 330              350
gac acc cgc cta cag ttg gcc atg gtc tgc tac agc cct gac ttt
Asp Thr Arg Leu Gln Leu Ala Met Val Cys Tyr Ser Pro Asp Phe 370              390
gag aga aag aag cca gag tac tta gag ggt ctc cct gag aag atg
Glu Arg Lys Lys Pro Glu Tyr Leu Glu Gly Leu Pro Glu Lys Met 410              430              450
aag ctt tac tcc gaa ttc ctg ggc aag cag cca tgg ttt gca ggg
Lys Leu Tyr Ser Glu Phe Leu Gly Lys Gln Pro Trp Phe Ala Gly 470              490
aac aag att acg tat gtg gat ttt ctt gtt tac gat gtc ctt gat
Asn Lys Ile Thr Tyr Val Asp Phe Leu Val Tyr Asp Val Leu Asp 510              530
caa cac cgt ata ttt gaa ccc aag tgc ctg gac gcc ttc cca aac
Gln His Arg Ile Phe Glu Pro Lys Cys Leu Asp Ala Phe Pro Asn 550              570
ctg aag gac ttc gtg gct cgg ttt gag ggc ctg aag aag ata tct
Leu Lys Asp Phe Val Ala Arg Phe Glu Gly Leu Lys Lys Ile Ser 590              610              630
gac tac atg aag agc ggc cgc ttc ctc tcc aag cca atc ttt gca
Asp Tyr Met Lys Ser Gly Arg Phe Leu Ser Lys Pro Ile Phe Ala 650
aag atg gcc ttt tgg aac cca aag tag
Lys Met Ala Phe Trp Asn Pro Lys End.
```

14. A recombinant DNA vector according to claim 11, wherein the genetic sequences comprises the following nucleotide sequence:

```
             30               50
atg cccatg aca ctg ggt tac tgg gac atccgt gggcta
MetProMetThrLeuGlyTyrTrpAspIle ArgGlyLeu 70               90
gcgcat gccatccgc ctg ctc ctg gaa tac aca gac tcgagctat gag
AlaHisAlaIle ArgLeuLeuLeuGluTyrThrAspSerSer TyrGlu 110              130              150
gagaag aga tac acc atg gga gac gct ccc gac ttt gac aga agccag tgg
GluLysArgTyrThrMetGlyAspAlaProAspPheAspArgSer GlnTrp 170              190
ctg aat gagaag ttc aaa ctg ggcctg gac ttc cccaat ctg ccctac
LeuAsnGluLysPheLysLeuGlyLeuAspPheProAsnLeuProTyr 210              230              250
tta att gat gga tca cacaag atcacc cag agcaat gccatcctg cgc tat
LeuIleAspGlySerHisLysIle ThrGlnSer AsnAlaIle LeuArgTyr 270              290
ctt ggccgc aag cacaac ctg tgt ggggagaca gaa gaggagagg attcgt
LeuGlyArgLysHisAsnLeuCysGlyGluThrGluGluGluArgIleArg 310              330              350
gtg gac attctg gagaat cagctc atg gac aac cgc atg gtgctg gcgaga
ValAspIleLeuGluAsnGlnLeuMetAspAsnArgMetValLeuAlaArg 370              390
ctt tgc tat aac cct gac ttt gagaag ctg aag cca gggtac ctg gag
LeuCysTyrAsnProAspPheGluLysLeuLysProGlyTyrLeuGlu 410              430              450
caa ctg cct ggaatg atg cgg ctt tac tccgagttc ctg ggcaag cgg cca
GlnLeuProGlyMetMetArgLeuTyrSerGluPheLeuGlyLysArgPro 470              490
ttg ttt gcaggggac aag atcacc ttt gtggat ttc attgct tac gat
TrpPheAlaGlyAspLysIle ThrPheValAspPheIle AlaTyrAsp
```

```
             510              530              550
gtt ctt gagagg aac caa gtg ttt gag gccacg tgc ctg gac gcgttc cca
ValLeuGluArgAsnGlnValPheGluAlaThrCysLeuAspAlaPhePro 570              590
aac ctg aag gat ttc atagcgcgc ttt gag ggcctg aag aag atctcc gac
AsnLeuLysAspPheIle AlaArgPheGluGlyLeuLysLysIle SerAsp 610              630              650
tac atg aag tccagccgc ttc ctc ccaaga cct ctg ttc aca aag atg gct
TyrMetLysSerSer ArgPheLeuProArgProLeuPheThrLysMetAla 670
aattgg ggcagcaag tag
Ile TrpGlySerLysEnd.
```

15. A recombinant DNA vector according to claim 11, wherein the plant promoter is selected from the group consisting of nos, ocs and CaMV promoters, the promoter of a soybean small subunit of ribulose bisphosphate carboxylase, and the promoter of a chlorophyll a/b binding protein.

16. A transformed dicotyledonous plant comprising a plant promoter operably linked to a genetic sequence coding for rat glutathione S-transferase, wherein said recombinant genetic sequence is capable of being expressed in the plant.

17. A plant according to claim 16, wherein the genetic sequences comprises the following nucleotide sequence:

```
             110              130
tac agc atg ggg gat gct ccc gac tat gac aga agc cag
Tyr Ser Met Gly Asp Ala Pro Asp Tyr Asp Arg Ser Gln 150              170
tgg ctg agt gag aag ttc aaa ctg ggc ctg gac ttc ccc aat ctg
Trp Leu Ser Glu Lys Phe Lys Leu Gly Leu Asp Phe Pro Asn Leu 190              210
ccc tac tta att gat ggg tca cac aag atc acc cag agc aat gcc
Pro Tyr Leu Ile Asp Gly Ser His Lys Ile Thr Gln Ser Asn Ala 230              250              270
atc ctg cgc tac ctt ggc cgg aag cac aac ctt tgt ggg gag aca
Ile Leu Arg Tyr Leu Gly Arg Lys His Asn Leu Cys Gly Glu Thr 290              310
gag gag gag agg att cgt gtg gac gtt ttg gag aac cag gct atg
Glu Glu Glu Arg Ile Arg Val Asp Val Leu Glu Asn Gln Ala Met 330              350
gac acc cgc cta cag ttg gcc atg gtc tgc tac agc cct gac ttt
Asp Thr Arg Leu Gln Leu Ala Met Val Cys Tyr Ser Pro Asp Phe 370              390
gag aga aag aag cca gag tac tta gag ggt ctc cct gag aag atg
Glu Arg Lys Lys Pro Glu Tyr Leu Glu Gly Leu Pro Glu Lys Met 410              430              450
aag ctt tac tcc gaa ttc ctg ggc aag cag cca tgg ttt gca ggg
Lys Leu Tyr Ser Glu Phe Leu Gly Lys Gln Pro Trp Phe Ala Gly 470              490
aac aag att acg tat gtg gat ttt ctt gtt tac gat gtc ctt gat
Asn Lys Ile Thr Tyr Val Asp Phe Leu Val Tyr Asp Val Leu Asp 510              530
caa cac cgt ata ttt gaa ccc aag tgc ctg gac gcc ttc cca aac
Gln His Arg Ile Phe Glu Pro Lys Cys Leu Asp Ala Phe Pro Asn 550              570
ctg aag gac ttc gtg gct cgg ttt gag ggc ctg aag aag ata tct
Leu Lys Asp Phe Val Ala Arg Phe Glu Gly Leu Lys Lys Ile Ser
```

```
590                 610                    630
gac tac atg aag agc ggc cgc ttc ctc tcc aag cca atc ttt gca
Asp Tyr Met Lys Ser Gly Arg Phe Leu Ser Lys Pro Ile Phe Ala 650
aag atg gcc ttt tgg aac cca aag tag
Lys Met Ala Phe Trp Asn Pro Lys End.
```

18. A plant according to claim 16, wherein the genetic sequences comprises the following nucleotide sequence:

```
10                  30
atg cct atg aca ctg ggt tac tgg gac atc cgt ggg ctg gct cac
Met Pro Met Thr Leu Gly Tyr Trp Asp Ile Arg Gly Leu Ala His 50                  70                  90
gcc att cgc ctg ttc ctg gag tat aca gac aca agc tat gag gac
Ala Ile Arg Leu Phe Leu Glu Tyr Thr Asp Thr Ser Tyr Glu Asp 110                 130
aag aag tac agc atg ggg gat gct ccc gac tat gac aga agc cag
Lys Lys Tyr Ser Met Gly Asp Ala Pro Asp Tyr Asp Arg Ser Gln 150                 170
tgg ctg agt gag aag ttc aaa ctg ggc ctg gac ttc ccc aat ctg
Trp Leu Ser Glu Lys Phe Lys Leu Gly Leu Asp Phe Pro Asn Leu 190                 210
ccc tac tta att gat ggg tca cac aag atc acc cag agc aat gcc
Pro Tyr Leu Ile Asp Gly Ser His Lys Ile Thr Gln Ser Asn Ala 230                 250                 270
atc ctg cgc tac ctt ggc cgg aag cac aac ctt tgt ggg gag aca
Ile Leu Arg Tyr Leu Gly Arg Lys His Asn Leu Cys Gly Glu Thr 290                 310
gag gag gag agg att cgt gtg gac gtt ttg gag aac cag gct atg
Glu Glu Glu Arg Ile Arg Val Asp Val Leu Glu Asn Gln Ala Met 330                 350
gac acc cgc cta cag ttg gcc atg gtc tgc tac agc cct gac ttt
Asp Thr Arg Leu Gln Leu Ala Met Val Cys Tyr Ser Pro Asp Phe 370                 390
gag aga aag aag cca gag tac tta gag ggt ctc cct gag aag atg
Glu Arg Lys Lys Pro Glu Tyr Leu Glu Gly Leu Pro Glu Lys Met 410                 430                 450
aag ctt tac tcc gaa ttc ctg ggc aag cag cca tgg ttt gca ggg
Lys Leu Tyr Ser Glu Phe Leu Gly Lys Gln Pro Trp Phe Ala Gly 470                 490
aac aag att acg tat gtg gat ttt ctt gtt tac gat gtc ctt gat
Asn Lys Ile Thr Tyr Val Asp Phe Leu Val Tyr Asp Val Leu Asp 510                 530
caa cac cgt ata ttt gaa ccc aag tgc ctg gac gcc ttc cca aac
Gln His Arg Ile Phe Glu Pro Lys Cys Leu Asp Ala Phe Pro Asn 550                 570
ctg aag gac ttc gtg gct cgg ttt gag ggc ctg aag aag ata tct
Leu Lys Asp Phe Val Ala Arg Phe Glu Gly Leu Lys Lys Ile Ser 590                 610                 630
gac tac atg aag agc ggc cgc ttc ctc tcc aag cca atc ttt gca
Asp Tyr Met Lys Ser Gly Arg Phe Leu Ser Lys Pro Ile Phe Ala 650
aag atg gcc ttt tgg aac cca aag tag
Lys Met Ala Phe Trp Asn Pro Lys End.
```

19. A plant according to claim 16, wherein the genetic sequences comprises the following nucleotide sequence:

```
        30                  50
atg ccc atg aca ctg ggt tac tgg gac atc cgt ggg cta gcg cat
Met Pro Met Thr Leu Gly Tyr Trp Asp Ile Arg Gly Leu Ala His 70                  90
gcc atc cgc ctg ctc ctg gaa tac aca gac tcg agc tat gag gag
Ala Ile Arg Leu Leu Leu Glu Tyr Thr Asp Ser Ser Tyr Glu Glu 110                 130
aag aga tac acc atg gga gac gct ccc gac ttt gac aga agc
Lys Arg Tyr Thr Met Gly Asp Ala Pro Asp Phe Asp Arg Ser 150                 170                 190
cag tgg ctg aat gag aag ttc aaa ctg ggc ctg gac ttc ccc aat
Gln Trp Leu Asn Glu Lys Phe Lys Leu Gly Leu Asp Phe Pro Asn 210                 230
ctg ccc tac tta att gat gga tca cac aag atc acc cag agc aat
Leu Pro Tyr Leu Ile Asp Gly Ser His Lys Ile Thr Gln Ser Asn 250                 270
gcc atc ctg cgc tat ctt ggc cgc aag cac aac ctg tgt ggg gag
Ala Ile Leu Arg Tyr Leu Gly Arg Lys His Asn Leu Cys Gly Glu 290                 310
aca gaa gag gag agg att cgt gtg gac att ctg gag aat cag ctc
Thr Glu Glu Glu Arg Ile Arg Val Asp Ile Leu Glu Asn Gln Leu 330                 350
atg gac aac cgc atg gtg ctg gcg aga ctt tgc tat aac cct
Met Asp Asn Arg Met Val Leu Ala Arg Leu Cys Tyr Asn Pro 370                 390                 410
gac ttt gag aag ctg aag cca ggg tac atg gag caa atg cct gga
Asp Phe Glu Lys Leu Lys Pro Gly Tyr Met Glu Gln Met Pro Gly 430                 450
atg atg cgg ctt tac tcc gag ttc ctg ggc aag cgg cca tgg ttt
Met Met Arg Leu Tyr Ser Glu Phe Leu Gly Lys Arg Pro Trp Phe 470                 490
gca ggg gac aag atc acc ttt gtg gat ttc att gct tac gat gtt
Ala Gly Asp Lys Ile Thr Phe Val Asp Phe Ile Ala Tyr Asp Val 510                 530
ctt gag agg aac caa gtg ttt gag gcc acg tgc ctg gac gcg ttc
Leu Glu Arg Asn Gln Val Phe Glu Ala Thr Cys Leu Asp Ala Phe 550                 570                 590
cca aac ctg aag gat ttc ata gcg cgc ttt gag ggc ctg aag aag
Pro Asn Leu Lys Asp Phe Ile Ala Arg Phe Glu Gly Leu Lys Lys 610                 630
atc tcc gac tac atg aag tcc agc cgc ttc ctc cca aga cct ctg
Ile Ser Asp Tyr Met Lys Ser Ser Arg Phe Leu Pro Arg Pro Leu 650                 670
ttc aca aag atg gct att tgg ggc agc aag tag
Phe Thr Lys Met Ala Ile Trp Gly Ser Lys End.
```

20. A plant according to claim 16, wherein the plant promoter is selected from the group consisting of nos, ocs and CaMV promoters, the promoter of a soybean small subunit of ribulose bis-phosphate carboxylase, and the promoter of a chlorophyll a/b binding protein.

21. Progeny of the plants of claim 16, wherein the progeny retains the expression of the recombinant genetic sequence.

22. Propagules regenerated from the plant of claim 16, wherein the propagule retains the expression of the recombinant genetic sequence.

23. A plant according to claim 16, wherein the plant exhibits resistance to those herbicides that are capable of being detoxified by glutathione S-transferase enzymes.

24. A plant according to claim 23, wherein the herbicide is a triazine.

* * * * *